United States Patent [19]
McKnight et al.

[11] Patent Number: 5,591,825
[45] Date of Patent: Jan. 7, 1997

[54] INTERLEUKIN 4 SIGNAL TRANSDUCERS

[75] Inventors: Steven L. McKnight; Jinzhao Hou, both of South San Francisco, Calif.

[73] Assignee: Tularik, Inc., So. San Francisco, Calif.

[21] Appl. No.: 276,099

[22] Filed: Jul. 15, 1994

Related U.S. Application Data

[63] Continuation-in-part of Ser. No. 269,604, Jul. 5, 1994, abandoned.

[51] Int. Cl.$^6$ .......................... C12N 15/12; C07K 14/47
[52] U.S. Cl. ...................... 530/350; 536/23.1; 536/23.5; 435/69.1; 435/6
[58] Field of Search ......................... 530/350; 536/23.5, 536/23.1; 435/69.1, 6

[56] References Cited

PUBLICATIONS

Darnell Jr. et al., "Jak–STAT Pathways and Transcriptional Activation in Response to IFNs and Other Extracellular Signaling Proteins", *Science* 264:1415–1421 (1994).

Greenlund et al., "Ligand–induced IFNγ Receptor Tyrosine Phosphorylation Couples the Receptor to its Signal Transduction System (p91)", *The EMBO Journal* 13(7):1591–1600 (1994).

Hou et al., "An Interleukin–4–induced Transcription Factor: IL–4 Stat", *Science* 265:1701–1706 (1994).

Köhler and Rieber, "Allergy–associated Iε and Fcε Receptor II (CD23b) Genes Activated via Binding of an Interleukin–4–induced Transcription Factor to a Novel Responsive Element", *Eur. J. Immunol.* 23:3066–3071 (1993).

Kotanides and Reich, "Requirement of Tyrosine Phosphorylation for Rapid Activation of a DNA Binding Factor by IL–4", *Science* 262:1265–1267 (1993).

Paul and Seder, "Lymphocyte Responses and Cytokines", *Cell* 76:241–251 (1994).

Schindler et al., "STF—IL–4: A Novel IL–4–induced Signal Transducing Factor", *The EMBO Journal* 13(6):1350–1356 (1994).

Shuai et al., "Activation of Transcription by IFN–γ: Tyrosine Phosphorylation of a 91–kD DNA Binding Protein", *Science* 258:1808–1812 (1992).

Shuai et al., "Interferon Activation of the Transcription Factor Stat91 Involves Dimerization through SH2–Phosphotyrosyl Peptide Interactions", *Cell* 76:821–828 (1994).

Yin et al. (1994) J. Biol. Chem, vol. 269, pp. 26614–26617.

*Primary Examiner*—John Ulm
*Assistant Examiner*—Prema Mertz
*Attorney, Agent, or Firm*—Flehr, Hohbach, Test, Albritton & Herbert

[57] ABSTRACT

The invention provides methods and compositions for identifying pharmacological agents useful in the diagnosis or treatment of disease associated with the expression of a gene modulated by an interleukin 4 signal transducer and activator of transcription, IL-4 Stat. IL-4 Stat peptides and IL-4 receptor peptides and nucleic acids encoding such peptides find therapeutic uses. The subject compositions include IL-4 Stat and IL-4 receptor proteins, portions thereof, nucleic acids encoding them, and specific antibodies. The disclosed pharmaceutical screening methods are particularly suited to high-throughput screening where one or more steps are performed by a computer controlled electromechanical robot comprising an axial rotatable arm.

3 Claims, No Drawings

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 3046 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 166..2706

( x i ) SEQUENCE DESCRIPTION: SEQ ID NO:1:

```
ATCTTATTTT  TCTTTTTGGT  GGTGGTGGTG  GAAGGGGGGA  GGTGCTAGCA  GGGCCAGCCT         60

TGAACTCGCT  GGACAGAGCT  ACAGACCTAT  GGGGCCTGGA  AGTGCCCGCT  GAGAAAGGGA        120

GAAGACAGCA  GAGGGGTTGC  CGAGGCAACC  TCCAAGTCCC  AGATC ATG TCT CTG             174
                                                  Met Ser Leu
                                                    1

TGG GGT CTG GTC TCC AAG ATG CCC CCA GAA AAA GTG CAG CGG CTC TAT             222
Trp Gly Leu Val Ser Lys Met Pro Pro Glu Lys Val Gln Arg Leu Tyr
      5              10                 15

GTC GAC TTT CCC CAA CAC CTG CGG CAT CTT CTG GGT GAC TGG CTG GAG             270
Val Asp Phe Pro Gln His Leu Arg His Leu Leu Gly Asp Trp Leu Glu
 20              25                  30                  35

AGC CAG CCC TGG GAG TTC CTG GTC GGC TCC GAC GCC TTC TGC TGC AAC             318
Ser Gln Pro Trp Glu Phe Leu Val Gly Ser Asp Ala Phe Cys Cys Asn
             40                  45                  50

TTG GCT AGT GCC CTA CTT TCA GAC ACT GTC CAG CAC CTT CAG GCC TCG             366
Leu Ala Ser Ala Leu Leu Ser Asp Thr Val Gln His Leu Gln Ala Ser
                 55                  60                  65

GTG GGA GAG CAG GGG GAG GGG AGC ACC ATC TTG CAA CAC ATC AGC ACC             414
Val Gly Glu Gln Gly Glu Gly Ser Thr Ile Leu Gln His Ile Ser Thr
         70                  75                  80

CTT GAG AGC ATA TAT CAG AGG GAC CCC CTG AAG CTG GTG GCC ACT TTC             462
Leu Glu Ser Ile Tyr Gln Arg Asp Pro Leu Lys Leu Val Ala Thr Phe
             85                  90                  95

AGA CAA ATA CTT CAA GGA GAG AAA AAA GCT GTT ATG GAA CAG TTC CGC             510
Arg Gln Ile Leu Gln Gly Glu Lys Lys Ala Val Met Glu Gln Phe Arg
100                 105                 110                 115

CAC TTG CCA ATG CCT TTC CAC TGG AAG CAG GAA GAA CTC AAG TTT AAG             558
His Leu Pro Met Pro Phe His Trp Lys Gln Glu Glu Leu Lys Phe Lys
                120                 125                 130

ACA GGC TTG CGG AGG CTG CAG CAC CGA GTA GGG GAG ATC CAC CTT CTC             606
Thr Gly Leu Arg Arg Leu Gln His Arg Val Gly Glu Ile His Leu Leu
                135                 140                 145
```

| | | | | | | | | | | | | | | | | |
|---|---|---|---|---|---|---|---|---|---|---|---|---|---|---|---|---|
| CGA | GAA | GCC | CTG | CAG | AAG | GGG | GCT | GAG | GCT | GGC | CAA | GTG | TCT | CTG | CAC | 654 |
| Arg | Glu | Ala | Leu | Gln | Lys | Gly | Ala | Glu | Ala | Gly | Gln | Val | Ser | Leu | His | |
| | | 150 | | | | | 155 | | | | 160 | | | | | |
| AGC | TTG | ATA | GAA | ACT | CCT | GCT | AAT | GGG | ACT | GGG | CCA | AGT | GAG | GCC | CTG | 702 |
| Ser | Leu | Ile | Glu | Thr | Pro | Ala | Asn | Gly | Thr | Gly | Pro | Ser | Glu | Ala | Leu | |
| | 165 | | | | 170 | | | | | 175 | | | | | | |
| GCC | ATG | CTA | CTG | CAG | GAG | ACC | ACT | GGA | GAG | CTA | GAG | GCA | GCC | AAA | GCC | 750 |
| Ala | Met | Leu | Leu | Gln | Glu | Thr | Thr | Gly | Glu | Leu | Glu | Ala | Ala | Lys | Ala | |
| 180 | | | | 185 | | | | | 190 | | | | | 195 | | |
| CTA | GTG | CTG | AAG | AGG | ATC | CAG | ATT | TGG | AAA | CGG | CAG | CAG | CAG | CTG | GCA | 798 |
| Leu | Val | Leu | Lys | Arg | Ile | Gln | Ile | Trp | Lys | Arg | Gln | Gln | Gln | Leu | Ala | |
| | | | | 200 | | | | | 205 | | | | | 210 | | |
| GGG | AAT | GGC | GCA | CCG | TTT | GAG | GAG | AGC | CTG | GCC | CCA | CTC | CAG | GAG | AGG | 846 |
| Gly | Asn | Gly | Ala | Pro | Phe | Glu | Glu | Ser | Leu | Ala | Pro | Leu | Gln | Glu | Arg | |
| | | | 215 | | | | | 220 | | | | | 225 | | | |
| TGT | GAA | AGC | CTG | GTG | GAC | ATT | TAT | TCC | CAG | CTA | CAG | CAG | GAG | GTA | GGG | 894 |
| Cys | Glu | Ser | Leu | Val | Asp | Ile | Tyr | Ser | Gln | Leu | Gln | Gln | Glu | Val | Gly | |
| | | 230 | | | | | 235 | | | | | 240 | | | | |
| GCG | GCT | GGT | GGG | GAG | CTT | GAG | CCC | AAG | ACC | CGG | GCA | TCG | CTG | ACT | GGC | 942 |
| Ala | Ala | Gly | Gly | Glu | Leu | Glu | Pro | Lys | Thr | Arg | Ala | Ser | Leu | Thr | Gly | |
| | 245 | | | | | 250 | | | | | 255 | | | | | |
| CGG | CTG | GAT | GAA | GTC | CTG | AGA | ACC | CTC | GTC | ACC | AGT | TGC | TTC | CTG | GTG | 990 |
| Arg | Leu | Asp | Glu | Val | Leu | Arg | Thr | Leu | Val | Thr | Ser | Cys | Phe | Leu | Val | |
| 260 | | | | | 265 | | | | | 270 | | | | | 275 | |
| GAG | AAG | CAG | CCC | CCC | CAG | GTA | CTG | AAG | ACT | CAG | ACC | AAG | TTC | CAG | GCT | 1038 |
| Glu | Lys | Gln | Pro | Pro | Gln | Val | Leu | Lys | Thr | Gln | Thr | Lys | Phe | Gln | Ala | |
| | | | | 280 | | | | | 285 | | | | | 290 | | |
| GGA | GTT | CGA | TTC | CTG | TTG | GGC | TTG | AGG | TTC | CTG | GGG | GCC | CCA | GCC | AAG | 1086 |
| Gly | Val | Arg | Phe | Leu | Leu | Gly | Leu | Arg | Phe | Leu | Gly | Ala | Pro | Ala | Lys | |
| | | 295 | | | | | 300 | | | | | 305 | | | | |
| CCT | CCG | CTG | GTC | AGG | GCC | GAC | ATG | GTG | ACA | GAG | AAG | CAG | GCG | CGG | GAG | 1134 |
| Pro | Pro | Leu | Val | Arg | Ala | Asp | Met | Val | Thr | Glu | Lys | Gln | Ala | Arg | Glu | |
| | | 310 | | | | | 315 | | | | | 320 | | | | |
| CTG | AGT | GTG | CCT | CAG | GGT | CCT | GGG | GCT | GGA | GCA | GAA | AGC | ACT | GGA | GAA | 1182 |
| Leu | Ser | Val | Pro | Gln | Gly | Pro | Gly | Ala | Gly | Ala | Glu | Ser | Thr | Gly | Glu | |
| | 325 | | | | | 330 | | | | | 335 | | | | | |
| ATC | ATC | AAC | AAC | ACT | GTG | CCC | TTG | GAG | AAC | AGC | ATT | CCT | GGG | AAC | TGC | 1230 |
| Ile | Ile | Asn | Asn | Thr | Val | Pro | Leu | Glu | Asn | Ser | Ile | Pro | Gly | Asn | Cys | |
| 340 | | | | | 345 | | | | | 350 | | | | | 355 | |
| TGC | TCT | GCC | CTG | TTC | AAG | AAC | CTG | CTT | CTC | AAG | AAG | ATC | AAG | CGG | TGT | 1278 |
| Cys | Ser | Ala | Leu | Phe | Lys | Asn | Leu | Leu | Leu | Lys | Lys | Ile | Lys | Arg | Cys | |
| | | | | 360 | | | | | 365 | | | | | 370 | | |
| GAG | CGG | AAG | GGC | ACT | GAG | TCT | GTC | ACA | GAG | GAG | AAG | TGC | GCT | GTG | CTC | 1326 |
| Glu | Arg | Lys | Gly | Thr | Glu | Ser | Val | Thr | Glu | Glu | Lys | Cys | Ala | Val | Leu | |
| | | | 375 | | | | | 380 | | | | | 385 | | | |
| TTC | TCT | GCC | AGC | TTC | ACA | CTT | GGC | CCC | GGC | AAA | CTC | CCC | ATC | CAG | CTC | 1374 |
| Phe | Ser | Ala | Ser | Phe | Thr | Leu | Gly | Pro | Gly | Lys | Leu | Pro | Ile | Gln | Leu | |
| | | 390 | | | | | 395 | | | | | 400 | | | | |
| CAG | GCC | CTG | TCT | CTG | CCC | CTG | GTG | GTC | ATC | GTC | CAT | GGC | AAC | CAA | GAC | 1422 |
| Gln | Ala | Leu | Ser | Leu | Pro | Leu | Val | Val | Ile | Val | His | Gly | Asn | Gln | Asp | |
| | 405 | | | | | 410 | | | | | 415 | | | | | |
| AAC | AAT | GCC | AAA | GCC | ACT | ATC | CTG | TGG | GAC | AAT | GCC | TTC | TCT | GAG | ATG | 1470 |
| Asn | Asn | Ala | Lys | Ala | Thr | Ile | Leu | Trp | Asp | Asn | Ala | Phe | Ser | Glu | Met | |
| 420 | | | | | 425 | | | | | 430 | | | | | 435 | |
| GAC | CGC | GTG | CCC | TTT | GTG | GTG | GCT | GAG | CGG | GTG | CCC | TGG | GAG | AAG | ATG | 1518 |
| Asp | Arg | Val | Pro | Phe | Val | Val | Ala | Glu | Arg | Val | Pro | Trp | Glu | Lys | Met | |
| | | | | 440 | | | | | 445 | | | | | 450 | | |
| TGT | GAA | ACT | CTG | AAC | CTG | AAG | TTC | ATG | GCT | GAG | GTG | GGG | ACC | AAC | CGG | 1566 |
| Cys | Glu | Thr | Leu | Asn | Leu | Lys | Phe | Met | Ala | Glu | Val | Gly | Thr | Asn | Arg | |
| | | | 455 | | | | | 460 | | | | | 465 | | | |

| | | | | | | | | | | | | | | | | |
|---|---|---|---|---|---|---|---|---|---|---|---|---|---|---|---|---|
| GGG | CTG | CTC | CCA | GAG | CAC | TTC | CTC | TTC | CTG | GCC | CAG | AAG | ATC | TTC | AAT | 1614 |
| Gly | Leu | Leu | Pro | Glu | His | Phe | Leu | Phe | Leu | Ala | Gln | Lys | Ile | Phe | Asn | |
| | | 470 | | | | 475 | | | | | | 480 | | | | |
| GAC | AAC | AGC | CTC | AGT | ATG | GAG | GCC | TTC | CAG | CAC | CGT | TCT | GTG | TCC | TGG | 1662 |
| Asp | Asn | Ser | Leu | Ser | Met | Glu | Ala | Phe | Gln | His | Arg | Ser | Val | Ser | Trp | |
| | 485 | | | | | 490 | | | | | 495 | | | | | |
| TCG | CAG | TTC | AAC | AAG | GAG | ATC | CTG | CTG | GGC | CGT | GGC | TTC | ACC | TTT | TGG | 1710 |
| Ser | Gln | Phe | Asn | Lys | Glu | Ile | Leu | Leu | Gly | Arg | Gly | Phe | Thr | Phe | Trp | |
| 500 | | | | | 505 | | | | | 510 | | | | | 515 | |
| CAG | TGG | TTT | GAT | GGT | GTC | CTG | GAC | CTC | ACC | AAA | CGC | TGT | CTC | CGG | AGC | 1758 |
| Gln | Trp | Phe | Asp | Gly | Val | Leu | Asp | Leu | Thr | Lys | Arg | Cys | Leu | Arg | Ser | |
| | | | | 520 | | | | | 525 | | | | | 530 | | |
| TAC | TGG | TCT | GAC | CGG | CTG | ATC | ATT | GGC | TTC | ATC | AGC | AAA | CAG | TAC | GTT | 1806 |
| Tyr | Trp | Ser | Asp | Arg | Leu | Ile | Ile | Gly | Phe | Ile | Ser | Lys | Gln | Tyr | Val | |
| | | | 535 | | | | | 540 | | | | | 545 | | | |
| ACT | AGC | CTT | CTT | CTC | AAT | GAG | CCC | GAC | GGA | ACC | TTT | CTC | CTC | CGC | TTC | 1854 |
| Thr | Ser | Leu | Leu | Leu | Asn | Glu | Pro | Asp | Gly | Thr | Phe | Leu | Leu | Arg | Phe | |
| | | 550 | | | | 555 | | | | | 560 | | | | | |
| AGC | GAC | TCA | GAG | ATT | GGG | GGC | ATC | ACC | ATT | GCC | CAT | GTC | ATC | CGG | GGC | 1902 |
| Ser | Asp | Ser | Glu | Ile | Gly | Gly | Ile | Thr | Ile | Ala | His | Val | Ile | Arg | Gly | |
| | 565 | | | | | 570 | | | | | 575 | | | | | |
| CAG | GAT | GGC | TCT | CCA | CAG | ATA | GAG | AAC | ATC | CAG | CCA | TTC | TCT | GCC | AAA | 1950 |
| Gln | Asp | Gly | Ser | Pro | Gln | Ile | Glu | Asn | Ile | Gln | Pro | Phe | Ser | Ala | Lys | |
| 580 | | | | | 585 | | | | | 590 | | | | | 595 | |
| GAC | CTG | TCC | ATT | CGC | TCA | CTG | GGG | GAC | CGA | ATC | CGG | GAT | CTT | GCT | CAG | 1998 |
| Asp | Leu | Ser | Ile | Arg | Ser | Leu | Gly | Asp | Arg | Ile | Arg | Asp | Leu | Ala | Gln | |
| | | | | 600 | | | | | 605 | | | | | 610 | | |
| CTC | AAA | AAT | CTC | TAT | CCC | AAG | AAG | CCC | AAG | GAT | GAG | GCT | TTC | CGG | AGC | 2046 |
| Leu | Lys | Asn | Leu | Tyr | Pro | Lys | Lys | Pro | Lys | Asp | Glu | Ala | Phe | Arg | Ser | |
| | | | 615 | | | | | 620 | | | | | 625 | | | |
| CAC | TAC | AAG | CCT | GAA | CAG | ATG | GGT | AAG | GAT | GGC | AGG | GGT | TAT | GTC | CCA | 2094 |
| His | Tyr | Lys | Pro | Glu | Gln | Met | Gly | Lys | Asp | Gly | Arg | Gly | Tyr | Val | Pro | |
| | | 630 | | | | 635 | | | | | 640 | | | | | |
| GCT | ACC | ATC | AAG | ATG | ACC | GTG | GAA | AGG | GAC | CAA | CCA | CTT | CCT | ACC | CCA | 2142 |
| Ala | Thr | Ile | Lys | Met | Thr | Val | Glu | Arg | Asp | Gln | Pro | Leu | Pro | Thr | Pro | |
| | 645 | | | | | 650 | | | | | 655 | | | | | |
| GAG | CTC | CAG | ATG | CCT | ACC | ATG | GTG | CCT | TCT | TAT | GAC | CTT | GGA | ATG | GCC | 2190 |
| Glu | Leu | Gln | Met | Pro | Thr | Met | Val | Pro | Ser | Tyr | Asp | Leu | Gly | Met | Ala | |
| 660 | | | | | 665 | | | | | 670 | | | | | 675 | |
| CCT | GAT | TCC | TCC | ATG | AGC | ATG | CAG | CTT | GGC | CCA | GAT | ATG | GTG | CCC | CAG | 2238 |
| Pro | Asp | Ser | Ser | Met | Ser | Met | Gln | Leu | Gly | Pro | Asp | Met | Val | Pro | Gln | |
| | | | | 680 | | | | | 685 | | | | | 690 | | |
| GTG | TAC | CCA | CCA | CAC | TCT | CAC | TCC | ATC | CCC | CCG | TAT | CAA | GGC | CTC | TCC | 2286 |
| Val | Tyr | Pro | Pro | His | Ser | His | Ser | Ile | Pro | Pro | Tyr | Gln | Gly | Leu | Ser | |
| | | | 695 | | | | | 700 | | | | | 705 | | | |
| CCA | GAA | GAA | TCA | GTC | AAC | GTG | TTG | TCA | GCC | TTC | CAG | GAG | CCT | CAC | CTG | 2334 |
| Pro | Glu | Glu | Ser | Val | Asn | Val | Leu | Ser | Ala | Phe | Gln | Glu | Pro | His | Leu | |
| | | 710 | | | | 715 | | | | | 720 | | | | | |
| CAG | ATG | CCC | CCC | AGC | CTG | GGC | CAG | ATG | AGC | CTG | CCC | TTT | GAC | CAG | CCT | 2382 |
| Gln | Met | Pro | Pro | Ser | Leu | Gly | Gln | Met | Ser | Leu | Pro | Phe | Asp | Gln | Pro | |
| | 725 | | | | | 730 | | | | | 735 | | | | | |
| CAC | CCC | CAG | GGC | CTG | CTG | CCG | TGC | CAG | CCT | CAG | GAG | CAT | GCT | GTG | TCC | 2430 |
| His | Pro | Gln | Gly | Leu | Leu | Pro | Cys | Gln | Pro | Gln | Glu | His | Ala | Val | Ser | |
| 740 | | | | | 745 | | | | | 750 | | | | | 755 | |
| AGC | CCT | GAC | CCC | CTG | CTC | TGC | TCA | GAT | GTG | ACC | ATG | GTG | GAA | GAC | AGC | 2478 |
| Ser | Pro | Asp | Pro | Leu | Leu | Cys | Ser | Asp | Val | Thr | Met | Val | Glu | Asp | Ser | |
| | | | | 760 | | | | | 765 | | | | | 770 | | |
| TGC | CTG | AGC | CAG | CCA | GTG | ACA | GCG | TTT | CCT | CAG | GGC | ACT | TGG | ATT | GGT | 2526 |
| Cys | Leu | Ser | Gln | Pro | Val | Thr | Ala | Phe | Pro | Gln | Gly | Thr | Trp | Ile | Gly | |
| | | | 775 | | | | | 780 | | | | | 785 | | | |

| | | | | | | | | | | | | | | | |
|---|---|---|---|---|---|---|---|---|---|---|---|---|---|---|---|
| GAA | GAC | ATA | TTC | CCT | CCT | CTG | CTG | CCT | CCC | ACT | GAA | CAG | GAC | CTC | ACT | 2574 |
| Glu | Asp | Ile 790 | Phe | Pro | Pro | Leu | Leu 795 | Pro | Pro | Thr | Glu | Gln 800 | Asp | Leu | Thr | |
| AAG | CTT | CTC | CTG | GAG | GGG | CAA | GGG | GAG | TCG | GGG | GGA | GGG | TCC | TTG | GGG | 2622 |
| Lys | Leu 805 | Leu | Leu | Glu | Gly | Gln 810 | Gly | Glu | Ser | Gly | Gly 815 | Gly | Ser | Leu | Gly | |
| GCA | CAG | CCC | CTC | CTG | CAG | CCC | TCC | CAC | TAT | GGG | CAA | TCT | GGG | ATC | TCA | 2670 |
| Ala 820 | Gln | Pro | Leu | Leu 825 | Gln | Pro | Ser | His | Tyr | Gly 830 | Gln | Ser | Gly | Ile | Ser 835 | |
| ATG | TCC | CAC | ATG | GAC | CTA | AGG | GCC | AAC | CCC | AGT | TGG | TGATCCCAGC | | | | 2716 |
| Met | Ser | His | Met | Asp 840 | Leu | Arg | Ala | Asn | Pro | Ser 845 | Trp | | | | | |

```
TGGAGGGAGA ACCCAAAGAG ACAGCTCTTC TACTACCCCC ACAGACCTGC TCTGGACACT   2776
TGCTCATGCC CTGCCAAGCA GCAGATGGGG AGGGTGCCCT CCTATCCCCA CCTACTCCTG   2836
GGTCAGGAGG AAAAGACTAA CAGGAGAATG CACAGTGGGT GGAGCCAATC CACTCCTTCC   2896
TTTCTATCAT TCCCCTGCCC ACCTCCTTCC AGCACTGACT GGAAGGGAAG TTCAGGCTCT   2956
GAGACACGCC CCAACATGCC TGCACCTGCA GCGCGCACAC GCACGCACAC ACACATACAG   3016
AGCTCTCTGA GGGTGATGGG GCTGAGCAGG                                    3046
```

( 2 ) INFORMATION FOR SEQ ID NO:2:

( i ) SEQUENCE CHARACTERISTICS:
( A ) LENGTH: 847 amino acids
( B ) TYPE: amino acid
( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met 1 | Ser | Leu | Trp | Gly 5 | Leu | Val | Ser | Lys | Met 10 | Pro | Pro | Glu | Lys | Val 15 | Gln |
| Arg | Leu | Tyr | Val 20 | Asp | Phe | Pro | Gln | His 25 | Leu | Arg | His | Leu | Leu 30 | Gly | Asp |
| Trp | Leu | Glu 35 | Ser | Gln | Pro | Trp | Glu 40 | Phe | Leu | Val | Gly | Ser 45 | Asp | Ala | Phe |
| Cys | Cys 50 | Asn | Leu | Ala | Ser | Ala 55 | Leu | Leu | Ser | Asp | Thr 60 | Val | Gln | His | Leu |
| Gln 65 | Ala | Ser | Val | Gly | Glu 70 | Gln | Gly | Glu | Gly | Ser 75 | Thr | Ile | Leu | Gln | His 80 |
| Ile | Ser | Thr | Leu | Glu 85 | Ser | Ile | Tyr | Gln | Arg 90 | Asp | Pro | Leu | Lys | Leu 95 | Val |
| Ala | Thr | Phe | Arg 100 | Gln | Ile | Leu | Gln | Gly 105 | Glu | Lys | Lys | Ala | Val 110 | Met | Glu |
| Gln | Phe | Arg 115 | His | Leu | Pro | Met | Pro 120 | Phe | His | Trp | Lys | Gln 125 | Glu | Glu | Leu |
| Lys | Phe 130 | Lys | Thr | Gly | Leu | Arg 135 | Arg | Leu | Gln | His | Arg 140 | Val | Gly | Glu | Ile |
| His 145 | Leu | Leu | Arg | Glu | Ala 150 | Leu | Gln | Lys | Gly | Ala 155 | Glu | Ala | Gly | Gln | Val 160 |
| Ser | Leu | His | Ser | Leu 165 | Ile | Glu | Thr | Pro | Ala 170 | Asn | Gly | Thr | Gly | Pro 175 | Ser |
| Glu | Ala | Leu | Ala 180 | Met | Leu | Leu | Gln | Glu 185 | Thr | Thr | Gly | Glu | Leu 190 | Glu | Ala |
| Ala | Lys | Ala 195 | Leu | Val | Leu | Lys | Arg 200 | Ile | Gln | Ile | Trp | Lys 205 | Arg | Gln | Gln |

```
Gln  Leu  Ala  Gly  Asn  Gly  Ala  Pro  Phe  Glu  Glu  Ser  Leu  Ala  Pro  Leu
     210                      215                      220

Gln  Glu  Arg  Cys  Glu  Ser  Leu  Val  Asp  Ile  Tyr  Ser  Gln  Leu  Gln  Gln
225                      230                      235                      240

Glu  Val  Gly  Ala  Ala  Gly  Gly  Glu  Leu  Glu  Pro  Lys  Thr  Arg  Ala  Ser
               245                      250                      255

Leu  Thr  Gly  Arg  Leu  Asp  Glu  Val  Leu  Arg  Thr  Leu  Val  Thr  Ser  Cys
               260                      265                      270

Phe  Leu  Val  Glu  Lys  Gln  Pro  Pro  Gln  Val  Leu  Lys  Thr  Gln  Thr  Lys
          275                      280                      285

Phe  Gln  Ala  Gly  Val  Arg  Phe  Leu  Leu  Gly  Leu  Arg  Phe  Leu  Gly  Ala
     290                      295                      300

Pro  Ala  Lys  Pro  Pro  Leu  Val  Arg  Ala  Asp  Met  Val  Thr  Glu  Lys  Gln
305                      310                      315                      320

Ala  Arg  Glu  Leu  Ser  Val  Pro  Gln  Gly  Pro  Gly  Ala  Gly  Ala  Glu  Ser
                    325                      330                      335

Thr  Gly  Glu  Ile  Ile  Asn  Asn  Thr  Val  Pro  Leu  Glu  Asn  Ser  Ile  Pro
               340                      345                      350

Gly  Asn  Cys  Cys  Ser  Ala  Leu  Phe  Lys  Asn  Leu  Leu  Leu  Lys  Lys  Ile
          355                      360                      365

Lys  Arg  Cys  Glu  Arg  Lys  Gly  Thr  Glu  Ser  Val  Thr  Glu  Glu  Lys  Cys
     370                      375                      380

Ala  Val  Leu  Phe  Ser  Ala  Ser  Phe  Thr  Leu  Gly  Pro  Gly  Lys  Leu  Pro
385                      390                      395                      400

Ile  Gln  Leu  Gln  Ala  Leu  Ser  Leu  Pro  Leu  Val  Val  Ile  Val  His  Gly
                    405                      410                      415

Asn  Gln  Asp  Asn  Asn  Ala  Lys  Ala  Thr  Ile  Leu  Trp  Asp  Asn  Ala  Phe
               420                      425                      430

Ser  Glu  Met  Asp  Arg  Val  Pro  Phe  Val  Val  Ala  Glu  Arg  Val  Pro  Trp
          435                      440                      445

Glu  Lys  Met  Cys  Glu  Thr  Leu  Asn  Leu  Lys  Phe  Met  Ala  Glu  Val  Gly
     450                      455                      460

Thr  Asn  Arg  Gly  Leu  Leu  Pro  Glu  His  Phe  Leu  Phe  Leu  Ala  Gln  Lys
465                      470                      475                      480

Ile  Phe  Asn  Asp  Asn  Ser  Leu  Ser  Met  Glu  Ala  Phe  Gln  His  Arg  Ser
                    485                      490                      495

Val  Ser  Trp  Ser  Gln  Phe  Asn  Lys  Glu  Ile  Leu  Leu  Gly  Arg  Gly  Phe
               500                      505                      510

Thr  Phe  Trp  Gln  Trp  Phe  Asp  Gly  Val  Leu  Asp  Leu  Thr  Lys  Arg  Cys
          515                      520                      525

Leu  Arg  Ser  Tyr  Trp  Ser  Asp  Arg  Leu  Ile  Ile  Gly  Phe  Ile  Ser  Lys
     530                      535                      540

Gln  Tyr  Val  Thr  Ser  Leu  Leu  Leu  Asn  Glu  Pro  Asp  Gly  Thr  Phe  Leu
545                      550                      555                      560

Leu  Arg  Phe  Ser  Asp  Ser  Glu  Ile  Gly  Gly  Ile  Thr  Ile  Ala  His  Val
                    565                      570                      575

Ile  Arg  Gly  Gln  Asp  Gly  Ser  Pro  Gln  Ile  Glu  Asn  Ile  Gln  Pro  Phe
               580                      585                      590

Ser  Ala  Lys  Asp  Leu  Ser  Ile  Arg  Ser  Leu  Gly  Asp  Arg  Ile  Arg  Asp
          595                      600                      605

Leu  Ala  Gln  Leu  Lys  Asn  Leu  Tyr  Pro  Lys  Lys  Pro  Lys  Asp  Glu  Ala
     610                      615                      620

Phe  Arg  Ser  His  Tyr  Lys  Pro  Glu  Gln  Met  Gly  Lys  Asp  Gly  Arg  Gly
625                      630                      635                      640
```

| | | | | | | | | | | | | | | | |
|---|---|---|---|---|---|---|---|---|---|---|---|---|---|---|---|
|Tyr|Val|Pro|Ala|Thr|Ile|Lys|Met|Thr|Val|Glu|Arg|Asp|Gln|Pro|Leu|
| | | | |645| | | |650| | | | |655| | |
|Pro|Thr|Pro|Glu|Leu|Gln|Met|Pro|Thr|Met|Val|Pro|Ser|Tyr|Asp|Leu|
| | | |660| | | |665| | | | |670| | | |
|Gly|Met|Ala|Pro|Asp|Ser|Ser|Met|Ser|Met|Gln|Leu|Gly|Pro|Asp|Met|
| | |675| | | |680| | | | |685| | | | |
|Val|Pro|Gln|Val|Tyr|Pro|Pro|His|Ser|His|Ser|Ile|Pro|Pro|Tyr|Gln|
| |690| | | |695| | | | |700| | | | | |
|Gly|Leu|Ser|Pro|Glu|Glu|Ser|Val|Asn|Val|Leu|Ser|Ala|Phe|Gln|Glu|
|705| | | |710| | | |715| | | | | | |720|
|Pro|His|Leu|Gln|Met|Pro|Pro|Ser|Leu|Gly|Gln|Met|Ser|Leu|Pro|Phe|
| | | |725| | | |730| | | | |735| | | |
|Asp|Gln|Pro|His|Pro|Gln|Gly|Leu|Leu|Pro|Cys|Gln|Pro|Gln|Glu|His|
| | |740| | | |745| | | | |750| | | | |
|Ala|Val|Ser|Ser|Pro|Asp|Pro|Leu|Leu|Cys|Ser|Asp|Val|Thr|Met|Val|
| |755| | | |760| | | | |765| | | | | |
|Glu|Asp|Ser|Cys|Leu|Ser|Gln|Pro|Val|Thr|Ala|Phe|Pro|Gln|Gly|Thr|
|770| | | |775| | | |780| | | | | | | |
|Trp|Ile|Gly|Glu|Asp|Ile|Phe|Pro|Pro|Leu|Leu|Pro|Pro|Thr|Glu|Gln|
|785| | | |790| | | |795| | | | | | |800|
|Asp|Leu|Thr|Lys|Leu|Leu|Leu|Glu|Gly|Gln|Gly|Glu|Ser|Gly|Gly|Gly|
| | | |805| | | |810| | | | |815| | | |
|Ser|Leu|Gly|Ala|Gln|Pro|Leu|Leu|Gln|Pro|Ser|His|Tyr|Gly|Gln|Ser|
| | |820| | | |825| | | | |830| | | | |
|Gly|Ile|Ser|Met|Ser|His|Met|Asp|Leu|Arg|Ala|Asn|Pro|Ser|Trp| |
| | |835| | | |840| | | | |845| | | | |

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

GTATTTCCCA GAAAAGGAAC      20

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:4:

CTCTTACCTG AGAAATGG      18

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:5:

GAATTTCTAA GAAAGGG 17

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:6:

ACATTCACAT GAAGTA 16

( 2 ) INFORMATION FOR SEQ ID NO:7:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:7:

AACTTCCCAA GAACAG 16

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:8:

AAGGTTTCAG AAGGG 15

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:9:

CCTTCCCCTA GCAACAG 17

( 2 ) INFORMATION FOR SEQ ID NO:10:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Gly Pro Pro Gly Glu Ala Gly Tyr Lys Ala Phe Ser Ser Leu Leu
 1              5                    10                  15

( 2 ) INFORMATION FOR SEQ ID NO:11:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Ala  Ser  Ser  Gly  Glu  Glu  Gly  Tyr  Lys  Pro  Phe  Gln  Asp  Leu  Ile
 1              5                        10                       15
```

( 2 ) INFORMATION FOR SEQ ID NO:12:

( i ) SEQUENCE CHARACTERISTICS:
        ( A ) LENGTH: 740 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Met  Ser  Gln  Trp  Tyr  Glu  Leu  Gln  Gln  Leu  Asp  Ser  Lys  Phe  Leu  Glu
 1              5                        10                       15

Gln  Val  His  Gln  Leu  Tyr  Asp  Asp  Ser  Phe  Pro  Met  Glu  Ile  Arg  Gln
               20                       25                       30

Tyr  Leu  Ala  Gln  Trp  Leu  Glu  Lys  Gln  Asp  Trp  Glu  His  Ala  Ala  Asn
               35                       40                       45

Asp  Val  Ser  Phe  Ala  Thr  Ile  Arg  Phe  His  Asp  Leu  Leu  Ser  Gln  Leu
     50                       55                       60

Asp  Asp  Gln  Tyr  Ser  Arg  Phe  Ser  Leu  Glu  Asn  Asn  Phe  Leu  Leu  Gln
65                       70                       75                       80

His  Asn  Ile  Arg  Lys  Ser  Lys  Arg  Asn  Leu  Gln  Asp  Asn  Phe  Gln  Glu
                    85                       90                       95

Asp  Pro  Ile  Gln  Met  Ser  Met  Ile  Ile  Tyr  Ser  Cys  Leu  Lys  Glu  Glu
               100                      105                      110

Arg  Lys  Ile  Leu  Glu  Asn  Ala  Gln  Arg  Phe  Asn  Gln  Ala  Gln  Ser  Gly
               115                      120                      125

Asn  Ile  Gln  Ser  Thr  Val  Met  Leu  Asp  Lys  Gln  Lys  Glu  Leu  Asp  Ser
     130                      135                      140

Lys  Val  Arg  Asn  Val  Lys  Asp  Lys  Val  Met  Cys  Ile  Glu  His  Glu  Ile
145                      150                      155                      160

Lys  Ser  Leu  Glu  Asp  Leu  Gln  Asp  Glu  Tyr  Asp  Phe  Lys  Cys  Lys  Thr
               165                      170                      175

Leu  Gln  Asn  Arg  Glu  His  Glu  Thr  Asn  Gly  Val  Ala  Lys  Ser  Asp  Gln
               180                      185                      190

Lys  Gln  Glu  Gln  Leu  Leu  Leu  Lys  Lys  Met  Tyr  Leu  Met  Leu  Asp  Asn
     195                      200                      205

Lys  Arg  Lys  Glu  Val  Val  His  Lys  Ile  Ile  Glu  Leu  Leu  Asn  Val  Thr
     210                      215                      220

Glu  Leu  Thr  Gln  Asn  Ala  Leu  Ile  Asn  Asp  Glu  Leu  Val  Glu  Trp  Lys
225                      230                      235                      240

Arg  Arg  Gln  Gln  Ser  Ala  Cys  Ile  Gly  Gly  Pro  Pro  Asn  Ala  Cys  Leu
               245                      250                      255

Asp  Gln  Leu  Gln  Gln  Val  Arg  Gln  Gln  Leu  Lys  Lys  Leu  Glu  Glu  Leu
               260                      265                      270
```

| | | | | | | | | | | | | |
|---|---|---|---|---|---|---|---|---|---|---|---|---|
| Glu | Gln | Lys | Tyr | Thr | Tyr | Glu | His | Asp | Pro | Ile | Thr | Lys | Asn | Lys | Gln |
| | | 275 | | | | | 280 | | | | | 285 | | | |
| Val | Leu | Trp | Asp | Arg | Thr | Phe | Ser | Leu | Phe | Gln | Gln | Leu | Ile | Gln | Ser |
| | | 290 | | | | 295 | | | | | 300 | | | | |
| Ser | Phe | Val | Val | Glu | Arg | Gln | Pro | Cys | Met | Pro | Thr | His | Pro | Gln | Arg |
| 305 | | | | | 310 | | | | | 315 | | | | | 320 |
| Pro | Leu | Val | Leu | Lys | Thr | Gly | Val | Gln | Phe | Thr | Val | Lys | Leu | Arg | Leu |
| | | | | 325 | | | | | 330 | | | | | 335 | |
| Leu | Val | Lys | Leu | Gln | Glu | Leu | Asn | Tyr | Asn | Leu | Lys | Val | Lys | Val | Leu |
| | | | 340 | | | | | 345 | | | | | 350 | | |
| Phe | Asp | Lys | Asp | Val | Asn | Glu | Arg | Asn | Thr | Val | Lys | Gly | Phe | Arg | Lys |
| | | 355 | | | | | 360 | | | | | 365 | | | |
| Phe | Asn | Ile | Leu | Gly | Thr | His | Thr | Lys | Val | Met | Asn | Met | Glu | Glu | Ser |
| | 370 | | | | | 375 | | | | | 380 | | | | |
| Thr | Asn | Gly | Ser | Leu | Ala | Ala | Glu | Phe | Arg | His | Leu | Gln | Leu | Lys | Glu |
| 385 | | | | | 390 | | | | | 395 | | | | | 400 |
| Gln | Lys | Asn | Ala | Gly | Thr | Arg | Thr | Asn | Glu | Gly | Pro | Leu | Ile | Val | Thr |
| | | | | 405 | | | | | 410 | | | | | 415 | |
| Glu | Glu | Leu | His | Ser | Leu | Ser | Phe | Glu | Thr | Gln | Leu | Cys | Gln | Pro | Gly |
| | | | 420 | | | | | 425 | | | | | 430 | | |
| Leu | Val | Ile | Asp | Leu | Glu | Thr | Thr | Ser | Leu | Pro | Val | Val | Val | Ile | Ser |
| | | 435 | | | | | 440 | | | | | 445 | | | |
| Asn | Val | Ser | Gln | Leu | Pro | Ser | Gly | Trp | Ala | Ser | Ile | Leu | Trp | Tyr | Asn |
| | 450 | | | | | 455 | | | | | 460 | | | | |
| Met | Leu | Val | Ala | Glu | Pro | Arg | Asn | Leu | Ser | Phe | Phe | Leu | Thr | Pro | Pro |
| 465 | | | | | 470 | | | | | 475 | | | | | 480 |
| Cys | Ala | Arg | Trp | Ala | Gln | Leu | Ser | Glu | Val | Leu | Ser | Trp | Gln | Phe | Ser |
| | | | | 485 | | | | | 490 | | | | | 495 | |
| Ser | Val | Thr | Lys | Arg | Gly | Leu | Asn | Val | Asp | Gln | Leu | Asn | Met | Leu | Gly |
| | | | | 500 | | | | | 505 | | | | | 510 | |
| Glu | Lys | Leu | Leu | Gly | Pro | Asn | Ala | Ser | Pro | Asp | Gly | Leu | Ile | Pro | Trp |
| | | | 515 | | | | | 520 | | | | | 525 | | |
| Thr | Arg | Phe | Cys | Lys | Glu | Asn | Ile | Asn | Asp | Lys | Asn | Phe | Pro | Phe | Trp |
| | | 530 | | | | | 535 | | | | | 540 | | | |
| Leu | Trp | Ile | Glu | Ser | Ile | Leu | Glu | Leu | Ile | Lys | Lys | His | Leu | Leu | Pro |
| 545 | | | | | 550 | | | | | 555 | | | | | 560 |
| Leu | Trp | Asn | Asp | Gly | Cys | Ile | Met | Gly | Phe | Ile | Ser | Lys | Glu | Arg | Glu |
| | | | | 565 | | | | | 570 | | | | | 575 | |
| Arg | Ala | Leu | Leu | Lys | Asp | Gln | Gln | Pro | Gly | Thr | Phe | Leu | Leu | Arg | Phe |
| | | | 580 | | | | | 585 | | | | | 590 | | |
| Ser | Glu | Ser | Ser | Arg | Glu | Gly | Ala | Ile | Thr | Phe | Thr | Trp | Val | Glu | Arg |
| | | 595 | | | | | 600 | | | | | 605 | | | |
| Ser | Gln | Asn | Gly | Gly | Glu | Pro | Asp | Phe | His | Ala | Val | Glu | Pro | Tyr | Thr |
| | 610 | | | | | 615 | | | | | 620 | | | | |
| Lys | Lys | Glu | Leu | Ser | Ala | Val | Thr | Phe | Pro | Asp | Ile | Ile | Arg | Asn | Tyr |
| 625 | | | | | 630 | | | | | 635 | | | | | 640 |
| Lys | Val | Met | Ala | Ala | Glu | Asn | Ile | Pro | Glu | Asn | Pro | Leu | Lys | Tyr | Leu |
| | | | | 645 | | | | | 650 | | | | | 655 | |
| Tyr | Pro | Asn | Ile | Asp | Lys | Asp | His | Ala | Phe | Gly | Lys | Tyr | Tyr | Ser | Arg |
| | | | 660 | | | | | 665 | | | | | 670 | | |
| Pro | Lys | Glu | Ala | Pro | Glu | Pro | Met | Glu | Leu | Asp | Gly | Pro | Lys | Gly | Thr |
| | | 675 | | | | | 680 | | | | | 685 | | | |
| Gly | Tyr | Ile | Lys | Thr | Glu | Leu | Ile | Ser | Val | Ser | Glu | Val | His | Pro | Ser |

```
               690                         695                      700
    Arg  Leu  Gln  Thr  Thr  Asp  Asn  Leu  Leu  Pro  Met  Ser  Pro  Glu  Glu  Phe
    705                      710                 715                          720

Asp  Glu  Val  Ser  Arg  Ile  Val  Gly  Ser  Val  Glu  Phe  Asp  Ser  Met  Met
                        725                      730                      735

Asn  Thr  Val  Xaa
                   740
```

( 2 ) INFORMATION FOR SEQ ID NO:13:

( i ) SEQUENCE CHARACTERISTICS:
        ( A ) LENGTH: 852 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
    Met  Ala  Gln  Trp  Glu  Met  Leu  Gln  Asn  Leu  Asp  Ser  Pro  Phe  Gln  Asp
    1                   5                   10                          15

Gln  Leu  His  Gln  Leu  Tyr  Ser  His  Ser  Leu  Leu  Pro  Val  Asp  Ile  Arg
                        20                  25                  30

Gln  Tyr  Leu  Ala  Val  Trp  Ile  Glu  Asp  Gln  Asn  Trp  Gln  Glu  Ala  Ala
                   35                  40                  45

Leu  Gly  Ser  Asp  Asp  Ser  Lys  Ala  Thr  Met  Leu  Phe  Phe  His  Phe  Leu
         50                  55                  60

Asp  Gln  Leu  Asn  Tyr  Glu  Cys  Gly  Arg  Cys  Ser  Gln  Asp  Pro  Glu  Ser
    65                  70                  75                           80

Leu  Leu  Leu  Gln  His  Asn  Leu  Arg  Lys  Phe  Cys  Arg  Asp  Ile  Gln  Pro
                        85                  90                  95

Phe  Ser  Gln  Asp  Pro  Thr  Gln  Leu  Ala  Glu  Met  Ile  Phe  Asn  Leu  Leu
                   100                 105                 110

Leu  Glu  Glu  Lys  Arg  Ile  Leu  Ile  Gln  Ala  Gln  Arg  Ala  Gln  Leu  Glu
              115                 120                 125

Gln  Gly  Glu  Pro  Val  Leu  Glu  Thr  Pro  Val  Glu  Ser  Gln  Gln  His  Glu
         130                 135                 140

Ile  Glu  Ser  Arg  Ile  Leu  Asp  Leu  Arg  Ala  Met  Met  Glu  Lys  Leu  Val
    145                 150                 155                          160

Lys  Ser  Ile  Ser  Gln  Leu  Lys  Asp  Gln  Asp  Val  Phe  Cys  Phe  Arg
                   165                 170                 175

Tyr  Lys  Ile  Gln  Ala  Lys  Gly  Lys  Thr  Pro  Ser  Leu  Asp  Pro  His  Gln
                   180                 185                 190

Thr  Lys  Glu  Gln  Lys  Ile  Leu  Gln  Glu  Thr  Leu  Asn  Glu  Leu  Asp  Lys
              195                 200                 205

Arg  Arg  Lys  Glu  Val  Leu  Asp  Ala  Ser  Lys  Ala  Leu  Leu  Gly  Arg  Leu
         210                 215                 220

Thr  Thr  Leu  Ile  Glu  Leu  Leu  Leu  Pro  Lys  Leu  Glu  Glu  Trp  Lys  Ala
    225                 230                 235                          240

Gln  Gln  Gln  Lys  Ala  Cys  Ile  Arg  Ala  Pro  Ile  Asp  His  Gly  Leu  Glu
                   245                 250                 255

Gln  Leu  Glu  Thr  Trp  Phe  Thr  Ala  Gly  Ala  Lys  Leu  Leu  Phe  His  Leu
                   260                 265                 270

Arg  Gln  Leu  Leu  Lys  Glu  Leu  Lys  Gly  Leu  Ser  Cys  Leu  Val  Ser  Tyr
              275                 280                 285

Gln  Asp  Asp  Pro  Leu  Thr  Lys  Gly  Val  Asp  Leu  Arg  Asn  Ala  Gln  Val
         290                 295                 300
```

```
Thr Glu Leu Leu Gln Arg Leu Leu His Arg Ala Phe Val Val Glu Thr
305                 310                 315                 320
Gln Pro Cys Met Pro Gln Thr Pro His Arg Pro Leu Ile Leu Lys Thr
                325                 330                 335
Gly Ser Lys Phe Thr Val Arg Thr Arg Leu Leu Val Arg Leu Gln Glu
            340                 345                 350
Gly Asn Glu Ser Leu Thr Val Glu Val Ser Ile Asp Arg Asn Pro Pro
        355                 360                 365
Gln Leu Gln Gly Phe Arg Lys Phe Asn Ile Leu Thr Ser Asn Gln Lys
    370                 375                 380
Thr Leu Thr Pro Glu Lys Gly Gln Ser Gln Gly Leu Ile Trp Asp Phe
385                 390                 395                 400
Gly Tyr Leu Thr Leu Val Glu Gln Arg Ser Gly Gly Ser Gly Lys Gly
                405                 410                 415
Ser Asn Lys Gly Pro Leu Gly Val Thr Glu Glu Leu His Ile Ile Ser
            420                 425                 430
Phe Thr Val Lys Tyr Thr Tyr Gln Gly Leu Lys Gln Glu Leu Lys Thr
        435                 440                 445
Asp Thr Leu Pro Val Val Ile Ile Ser Asn Met Asn Gln Leu Ser Ile
    450                 455                 460
Ala Trp Ala Ser Val Leu Trp Phe Asn Leu Leu Ser Pro Asn Leu Gln
465                 470                 475                 480
Asn Gln Gln Phe Phe Ser Asn Pro Pro Lys Ala Pro Trp Ser Leu Leu
                485                 490                 495
Gly Pro Ala Leu Ser Trp Gln Phe Ser Ser Tyr Val Gly Arg Gly Leu
            500                 505                 510
Asn Ser Asp Gln Leu Ser Met Leu Arg Asn Lys Leu Phe Gly Gln Asn
        515                 520                 525
Cys Arg Thr Glu Asp Pro Leu Leu Ser Trp Ala Asp Phe Thr Lys Arg
    530                 535                 540
Glu Ser Pro Pro Gly Lys Leu Pro Phe Trp Thr Trp Leu Asp Lys Ile
545                 550                 555                 560
Leu Glu Leu Val His Asp His Leu Lys Asp Leu Trp Asn Asp Gly Arg
                565                 570                 575
Ile Met Gly Phe Val Ser Arg Ser Gln Glu Arg Arg Leu Leu Lys Lys
            580                 585                 590
Thr Met Ser Gly Thr Phe Leu Leu Arg Phe Ser Glu Ser Ser Glu Gly
        595                 600                 605
Gly Ile Thr Cys Ser Trp Val Glu His Gln Asp Asp Asp Lys Val Leu
    610                 615                 620
Ile Tyr Ser Val Gln Pro Tyr Thr Lys Glu Val Leu Gln Ser Leu Pro
625                 630                 635                 640
Leu Thr Glu Ile Ile Arg His Tyr Gln Leu Leu Thr Glu Glu Asn Ile
                645                 650                 655
Pro Glu Asn Pro Leu Arg Phe Leu Tyr Pro Arg Ile Pro Arg Asp Glu
            660                 665                 670
Ala Phe Gly Cys Tyr Tyr Gln Glu Lys Val Asn Leu Gln Glu Arg Arg
        675                 680                 685
Lys Tyr Leu Lys His Arg Leu Ile Val Val Ser Asn Arg Gln Val Asp
    690                 695                 700
Glu Leu Gln Gln Pro Leu Glu Leu Lys Pro Glu Pro Glu Leu Glu Ser
705                 710                 715                 720
Leu Glu Leu Glu Leu Gly Leu Val Pro Glu Pro Glu Leu Ser Leu Asp
```

|     |     |     |     |     | 725 |     |     |     |     | 730 |     |     |     |     | 735 |
| --- | --- | --- | --- | --- | --- | --- | --- | --- | --- | --- | --- | --- | --- | --- | --- |
| Leu | Glu | Pro | Leu | Leu | Lys | Ala | Gly | Leu | Asp | Leu | Gly | Pro | Glu | Leu | Glu |
|     |     |     | 740 |     |     |     | 745 |     |     |     | 750 |     |     |     |     |
| Ser | Val | Leu | Glu | Ser | Thr | Leu | Glu | Pro | Val | Ile | Glu | Pro | Thr | Leu | Cys |
|     |     | 755 |     |     |     | 760 |     |     |     |     | 765 |     |     |     |     |
| Met | Val | Ser | Gln | Thr | Val | Pro | Glu | Pro | Asp | Gln | Gly | Pro | Val | Ser | Gln |
|     | 770 |     |     |     |     | 775 |     |     |     |     | 780 |     |     |     |     |
| Pro | Val | Pro | Glu | Pro | Asp | Leu | Pro | Cys | Asp | Leu | Arg | His | Leu | Asn | Thr |
| 785 |     |     |     |     | 790 |     |     |     |     | 795 |     |     |     |     | 800 |
| Glu | Pro | Met | Glu | Ile | Phe | Arg | Asn | Cys | Val | Lys | Ile | Glu | Glu | Ile | Met |
|     |     |     |     | 805 |     |     |     |     | 810 |     |     |     |     | 815 |     |
| Pro | Asn | Gly | Asp | Pro | Leu | Leu | Ala | Gly | Gln | Asn | Thr | Val | Asp | Glu | Val |
|     |     |     | 820 |     |     |     |     | 825 |     |     |     |     | 830 |     |     |
| Tyr | Val | Ser | Arg | Pro | Ser | His | Phe | Tyr | Thr | Asp | Gly | Pro | Leu | Met | Pro |
|     |     | 835 |     |     |     |     | 840 |     |     |     |     | 845 |     |     |     |
| Ser | Asp | Phe | Xaa |     |     |     |     |     |     |     |     |     |     |     |     |
|     |     | 850 |     |     |     |     |     |     |     |     |     |     |     |     |     |

( 2 ) INFORMATION FOR SEQ ID NO:14:

( i ) SEQUENCE CHARACTERISTICS:
        ( A ) LENGTH: 771 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Ala | Gln | Trp | Asn | Gln | Leu | Gln | Gln | Leu | Asp | Thr | Arg | Tyr | Leu | Glu |
| 1   |     |     |     | 5   |     |     |     |     | 10  |     |     |     |     | 15  |     |
| Gln | Leu | His | Gln | Leu | Tyr | Ser | Asp | Ser | Phe | Pro | Met | Glu | Leu | Arg | Gln |
|     |     |     | 20  |     |     |     |     | 25  |     |     |     |     | 30  |     |     |
| Phe | Leu | Ala | Pro | Trp | Ile | Glu | Ser | Gln | Asp | Trp | Ala | Tyr | Ala | Ala | Ser |
|     |     | 35  |     |     |     |     | 40  |     |     |     |     | 45  |     |     |     |
| Lys | Glu | Ser | His | Ala | Thr | Leu | Val | Phe | His | Asn | Leu | Leu | Gly | Glu | Ile |
|     | 50  |     |     |     |     | 55  |     |     |     |     | 60  |     |     |     |     |
| Asp | Gln | Gln | Tyr | Ser | Arg | Phe | Leu | Gln | Glu | Ser | Asn | Val | Leu | Tyr | Gln |
| 65  |     |     |     |     | 70  |     |     |     |     | 75  |     |     |     |     | 80  |
| His | Asn | Leu | Arg | Arg | Ile | Lys | Gln | Phe | Leu | Gln | Ser | Arg | Tyr | Leu | Glu |
|     |     |     |     | 85  |     |     |     |     | 90  |     |     |     |     | 95  |     |
| Lys | Pro | Met | Glu | Ile | Ala | Arg | Ile | Val | Ala | Arg | Cys | Leu | Trp | Glu | Glu |
|     |     |     | 100 |     |     |     |     | 105 |     |     |     |     | 110 |     |     |
| Ser | Arg | Leu | Leu | Gln | Thr | Ala | Ala | Thr | Ala | Ala | Gln | Gln | Gly | Gly | Gln |
|     |     | 115 |     |     |     |     | 120 |     |     |     |     | 125 |     |     |     |
| Ala | Asn | His | Pro | Thr | Ala | Ala | Val | Val | Thr | Glu | Lys | Gln | Gln | Met | Leu |
|     | 130 |     |     |     |     | 135 |     |     |     |     | 140 |     |     |     |     |
| Glu | Gln | His | Leu | Gln | Asp | Val | Arg | Lys | Arg | Val | Gln | Asp | Leu | Glu | Gln |
| 145 |     |     |     |     | 150 |     |     |     |     | 155 |     |     |     |     | 160 |
| Lys | Met | Lys | Val | Val | Glu | Asn | Leu | Gln | Asp | Asp | Phe | Asp | Phe | Asn | Tyr |
|     |     |     |     | 165 |     |     |     |     | 170 |     |     |     |     | 175 |     |
| Lys | Thr | Leu | Lys | Ser | Gln | Gly | Asp | Met | Gln | Asp | Leu | Asn | Gly | Asn | Asn |
|     |     |     | 180 |     |     |     |     | 185 |     |     |     |     | 190 |     |     |
| Gln | Ser | Val | Thr | Arg | Gln | Lys | Met | Gln | Gln | Leu | Glu | Gln | Met | Leu | Thr |
|     |     | 195 |     |     |     |     | 200 |     |     |     |     | 205 |     |     |     |
| Ala | Leu | Asp | Gln | Met | Arg | Arg | Ser | Ile | Val | Ser | Glu | Leu | Ala | Gly | Leu |
|     | 210 |     |     |     |     | 215 |     |     |     |     | 220 |     |     |     |     |

| | | | | | | | | | | | | | | | |
|---|---|---|---|---|---|---|---|---|---|---|---|---|---|---|---|
| Leu | Ser | Ala | Met | Glu | Tyr | Val | Gln | Lys | Thr | Leu | Thr | Asp | Glu | Glu | Leu |
| 225 | | | | 230 | | | | | 235 | | | | | | 240 |
| Ala | Asp | Trp | Lys | Arg | Arg | Gln | Gln | Ile | Ala | Cys | Ile | Gly | Gly | Pro | Pro |
| | | | | 245 | | | | | 250 | | | | | 255 | |
| Asn | Ile | Cys | Leu | Asp | Arg | Leu | Glu | Asn | Trp | Ile | Thr | Ser | Leu | Ala | Glu |
| | | | 260 | | | | | 265 | | | | | 270 | | |
| Ser | Gln | Leu | Gln | Thr | Arg | Gln | Gln | Ile | Lys | Lys | Leu | Glu | Glu | Leu | His |
| | | 275 | | | | | 280 | | | | | 285 | | | |
| Gln | Lys | Val | Ser | Tyr | Lys | Gly | Asp | Pro | Ile | Val | Gln | His | Arg | Pro | Met |
| | 290 | | | | | 295 | | | | | 300 | | | | |
| Leu | Glu | Glu | Arg | Ile | Val | Glu | Leu | Phe | Arg | Asn | Leu | Met | Lys | Ser | Ala |
| 305 | | | | | 310 | | | | | 315 | | | | | 320 |
| Phe | Val | Val | Glu | Arg | Gln | Pro | Cys | Met | Pro | Met | His | Pro | Asp | Arg | Pro |
| | | | | 325 | | | | | 330 | | | | | 335 | |
| Leu | Val | Ile | Lys | Thr | Gly | Val | Gln | Phe | Thr | Thr | Lys | Val | Arg | Leu | Leu |
| | | | 340 | | | | | 345 | | | | | 350 | | |
| Val | Lys | Phe | Pro | Glu | Leu | Asn | Tyr | Gln | Leu | Lys | Ile | Lys | Val | Cys | Ile |
| | | 355 | | | | | 360 | | | | | 365 | | | |
| Asp | Lys | Asp | Ser | Gly | Asp | Val | Ala | Ala | Leu | Arg | Gly | Ser | Arg | Lys | Phe |
| | 370 | | | | | 375 | | | | | 380 | | | | |
| Asn | Ile | Leu | Gly | Thr | Asn | Thr | Lys | Val | Met | Asn | Met | Glu | Glu | Ser | Asn |
| 385 | | | | | 390 | | | | | 395 | | | | | 400 |
| Asn | Gly | Ser | Leu | Ser | Ala | Glu | Phe | Lys | His | Leu | Thr | Leu | Arg | Glu | Gln |
| | | | | 405 | | | | | 410 | | | | | 415 | |
| Arg | Cys | Gly | Asn | Gly | Gly | Arg | Ala | Asn | Cys | Asp | Ala | Ser | Leu | Ile | Val |
| | | | 420 | | | | | 425 | | | | | 430 | | |
| Thr | Glu | Glu | Leu | His | Leu | Ile | Thr | Phe | Glu | Thr | Glu | Val | Tyr | His | Gln |
| | | 435 | | | | | 440 | | | | | 445 | | | |
| Gly | Leu | Lys | Ile | Asp | Leu | Glu | Thr | His | Ser | Leu | Ser | Val | Val | Val | Ile |
| | 450 | | | | | 455 | | | | | 460 | | | | |
| Ser | Asn | Ile | Cys | Gln | Met | Pro | Asn | Ala | Trp | Ala | Ser | Ile | Leu | Trp | Tyr |
| 465 | | | | | 470 | | | | | 475 | | | | | 480 |
| Asn | Met | Leu | Thr | Asn | Asn | Pro | Lys | Asn | Val | Asn | Phe | Phe | Thr | Lys | Pro |
| | | | | 485 | | | | | 490 | | | | | 495 | |
| Pro | Ile | Gly | Thr | Trp | Asp | Gln | Val | Ala | Glu | Val | Leu | Ser | Trp | Gln | Phe |
| | | | 500 | | | | | 505 | | | | | 510 | | |
| Ser | Ser | Thr | Thr | Lys | Arg | Gly | Leu | Ser | Ile | Glu | Gln | Leu | Thr | Thr | Leu |
| | | | 515 | | | | | 520 | | | | | 525 | | |
| Ala | Glu | Lys | Leu | Leu | Gly | Pro | Gly | Val | Asn | Tyr | Ser | Gly | Cys | Gln | Ile |
| | 530 | | | | | 535 | | | | | 540 | | | | |
| Thr | Trp | Ala | Asn | Phe | Cys | Lys | Glu | Asn | Met | Ala | Gly | Lys | Gly | Phe | Ser |
| 545 | | | | | 550 | | | | | 555 | | | | | 560 |
| Tyr | Trp | Val | Trp | Leu | Asp | Asn | Ile | Ile | Asp | Leu | Val | Lys | Lys | Tyr | Ile |
| | | | | 565 | | | | | 570 | | | | | 575 | |
| Leu | Ala | Leu | Trp | Asn | Glu | Gly | Tyr | Ile | Met | Gly | Phe | Ile | Ser | Lys | Glu |
| | | | 580 | | | | | 585 | | | | | 590 | | |
| Arg | Glu | Arg | Ala | Ile | Leu | Ser | Thr | Lys | Pro | Pro | Gly | Thr | Phe | Leu | Leu |
| | | 595 | | | | | 600 | | | | | 605 | | | |
| Arg | Phe | Ser | Glu | Ser | Ser | Lys | Glu | Gly | Gly | Val | Thr | Phe | Thr | Trp | Val |
| | 610 | | | | | 615 | | | | | 620 | | | | |
| Glu | Lys | Asp | Ile | Ser | Gly | Lys | Thr | Gln | Ile | Gln | Ser | Val | Glu | Pro | Tyr |
| 625 | | | | | 630 | | | | | 635 | | | | | 640 |
| Thr | Lys | Gln | Gln | Leu | Asn | Asn | Met | Ser | Phe | Ala | Glu | Ile | Ile | Met | Gly |

|     |     |     |     | 645 |     |     |     |     | 650 |     |     |     |     | 655 |     |     |
| --- | --- | --- | --- | --- | --- | --- | --- | --- | --- | --- | --- | --- | --- | --- | --- | --- |
| Tyr | Lys | Ile | Met | Asp | Ala | Thr | Asn | Ile | Leu | Leu | Ser | Pro | Leu | Val | Tyr |
|     |     |     | 660 |     |     |     | 665 |     |     |     | 670 |     |     |     |     |
| Leu | Tyr | Pro | Asp | Ile | Pro | Lys | Glu | Glu | Ala | Phe | Gly | Lys | Tyr | Cys | Arg |
|     |     | 675 |     |     |     |     | 680 |     |     |     | 685 |     |     |     |     |
| Pro | Glu | Ser | Gln | Glu | His | Pro | Glu | Ala | Asp | Pro | Gly | Ser | Ala | Ala | Pro |
|     | 690 |     |     |     |     | 695 |     |     |     | 700 |     |     |     |     |     |
| Tyr | Leu | Lys | Thr | Lys | Phe | Ile | Cys | Val | Thr | Pro | Thr | Thr | Cys | Ser | Asn |
| 705 |     |     |     |     | 710 |     |     |     |     | 715 |     |     |     |     | 720 |
| Thr | Ile | Asp | Leu | Pro | Met | Ser | Pro | Arg | Ala | Leu | Asp | Ser | Leu | Met | Gln |
|     |     |     |     | 725 |     |     |     |     | 730 |     |     |     | 735 |     |     |
| Phe | Gly | Asn | Asn | Gly | Glu | Gly | Ala | Glu | Pro | Ser | Ala | Gly | Gly | Gln | Phe |
|     |     |     | 740 |     |     |     |     | 745 |     |     |     |     | 750 |     |     |
| Glu | Ser | Leu | Thr | Phe | Asp | Met | Glu | Leu | Thr | Ser | Glu | Cys | Ala | Thr | Ser |
|     |     | 755 |     |     |     |     | 760 |     |     |     |     | 765 |     |     |     |
| Pro | Met | Xaa |
|     | 770 |     |

( 2 ) INFORMATION FOR SEQ ID NO:15:

( i ) SEQUENCE CHARACTERISTICS:
      ( A ) LENGTH: 749 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:15:

| Met | Ser | Gln | Trp | Asn | Gln | Val | Gln | Gln | Leu | Glu | Ile | Lys | Phe | Leu | Glu |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Gln | Val | Asp | Gln | Phe | Tyr | Asp | Asp | Phe | Pro | Met | Glu | Ile | Arg | His |
|     |     |     | 20  |     |     |     |     | 25  |     |     |     |     | 30  |     |
| Leu | Leu | Ala | Gln | Trp | Ile | Glu | Thr | Gln | Asp | Trp | Glu | Val | Ala | Ser | Asn |
|     |     |     | 35  |     |     |     |     | 40  |     |     |     |     | 45  |     |     |
| Asn | Glu | Thr | Met | Ala | Thr | Ile | Leu | Leu | Gln | Asn | Leu | Leu | Ile | Gln | Leu |
|     | 50  |     |     |     |     | 55  |     |     |     |     | 60  |     |     |     |     |
| Asp | Glu | Gln | Leu | Gly | Arg | Val | Ser | Lys | Glu | Lys | Asn | Leu | Leu | Leu | Ile |
| 65  |     |     |     |     | 70  |     |     |     |     | 75  |     |     |     |     | 80  |
| His | Asn | Leu | Lys | Arg | Ile | Arg | Lys | Val | Leu | Gln | Gly | Lys | Phe | His | Gly |
|     |     |     |     | 85  |     |     |     |     | 90  |     |     |     |     | 95  |     |
| Asn | Pro | Met | His | Val | Ala | Val | Val | Ile | Ser | Asn | Cys | Leu | Arg | Glu | Glu |
|     |     |     | 100 |     |     |     |     | 105 |     |     |     |     | 110 |     |     |
| Arg | Arg | Ile | Leu | Ala | Ala | Ala | Asn | Met | Pro | Ile | Gln | Gly | Pro | Leu | Glu |
|     |     |     | 115 |     |     |     |     | 120 |     |     |     |     | 125 |     |     |
| Lys | Ser | Leu | Gln | Ser | Ser | Ser | Val | Ser | Glu | Arg | Gln | Arg | Asn | Val | Glu |
|     |     | 130 |     |     |     |     | 135 |     |     |     |     | 140 |     |     |     |
| His | Lys | Val | Ser | Ala | Ile | Lys | Asn | Ser | Val | Gln | Met | Thr | Glu | Gln | Asp |
| 145 |     |     |     |     | 150 |     |     |     |     | 155 |     |     |     |     | 160 |
| Thr | Lys | Tyr | Leu | Glu | Asp | Leu | Gln | Asp | Glu | Phe | Asp | Tyr | Arg | Tyr | Lys |
|     |     |     |     | 165 |     |     |     |     | 170 |     |     |     |     | 175 |     |
| Thr | Ile | Gln | Thr | Met | Asp | Gln | Gly | Asp | Lys | Asn | Ser | Ile | Leu | Val | Asn |
|     |     |     | 180 |     |     |     |     | 185 |     |     |     |     | 190 |     |     |
| Gln | Glu | Val | Leu | Thr | Leu | Leu | Gln | Glu | Met | Leu | Asn | Ser | Leu | Asp | Phe |
|     |     |     | 195 |     |     |     |     | 200 |     |     |     |     | 205 |     |     |
| Lys | Arg | Lys | Glu | Ala | Leu | Ser | Lys | Met | Thr | Gln | Ile | Val | Asn | Glu | Thr |
|     |     | 210 |     |     |     |     | 215 |     |     |     |     | 220 |     |     |     |

```
Asp Leu Leu Met Asn Ser Met Leu Leu Glu Leu Gln Asp Trp Lys
225                 230                 235                 240

Lys Arg Gln Gln Ile Ala Cys Ile Gly Gly Pro Leu His Asn Gly Leu
            245                 250                 255

Asp Gln Leu Gln Asn Cys Phe Thr Leu Leu Ala Glu Ser Leu Phe Gln
                260                 265                 270

Leu Arg Gln Gln Leu Glu Lys Leu Gln Glu Gln Ser Thr Lys Met Thr
            275                 280                 285

Tyr Glu Gly Asp Pro Ile Pro Ala Gln Arg Ala His Leu Leu Glu Arg
    290                 295                 300

Ala Thr Phe Leu Ile Tyr Asn Leu Phe Lys Asn Ser Phe Val Val Glu
305                 310                 315                 320

Arg Gln Pro Cys Met Pro Thr His Pro Gln Arg Pro Met Val Leu Lys
                325                 330                 335

Thr Leu Ile Gln Phe Thr Val Lys Leu Arg Leu Leu Ile Lys Leu Pro
            340                 345                 350

Glu Leu Asn Tyr Gln Val Lys Val Lys Ala Ser Ile Asp Lys Asn Val
        355                 360                 365

Ser Thr Leu Ser Asn Arg Arg Phe Val Leu Cys Gly Thr His Val Lys
    370                 375                 380

Ala Met Ser Ser Glu Glu Ser Ser Asn Gly Ser Leu Ser Val Glu Phe
385                 390                 395                 400

Arg His Leu Gln Pro Lys Glu Met Lys Cys Ser Thr Gly Ser Lys Gly
                405                 410                 415

Asn Glu Gly Cys His Met Val Thr Glu Glu Leu His Ser Ile Thr Phe
            420                 425                 430

Glu Thr Gln Ile Cys Leu Tyr Gly Leu Thr Ile Asn Leu Glu Thr Ser
        435                 440                 445

Ser Leu Pro Val Val Met Ile Ser Asn Val Ser Gln Leu Pro Asn Ala
    450                 455                 460

Trp Ala Ser Ile Ile Trp Tyr Asn Val Ser Thr Asn Asp Ser Gln Asn
465                 470                 475                 480

Leu Val Phe Phe Asn Asn Pro Pro Ser Val Thr Leu Gly Gln Leu Leu
                485                 490                 495

Glu Val Met Ser Trp Gln Phe Ser Ser Tyr Val Gly Arg Gly Leu Asn
            500                 505                 510

Ser Glu Gln Leu Asn Met Leu Ala Glu Lys Leu Thr Val Gln Ser Asn
        515                 520                 525

Tyr Asn Asp Gly His Leu Thr Trp Ala Lys Phe Cys Lys Glu His Leu
    530                 535                 540

Pro Gly Lys Thr Phe Thr Phe Trp Thr Trp Leu Glu Ala Ile Leu Asp
545                 550                 555                 560

Leu Ile Lys Lys His Ile Leu Pro Leu Trp Ile Asp Gly Tyr Ile Met
                565                 570                 575

Gly Phe Val Ser Lys Glu Lys Glu Arg Leu Leu Leu Lys Asp Lys Met
            580                 585                 590

Pro Gly Thr Phe Leu Leu Arg Phe Ser Glu Ser His Leu Gly Gly Ile
        595                 600                 605

Thr Phe Thr Trp Val Asp Gln Ser Glu Asn Gly Glu Val Arg Phe His
    610                 615                 620

Ser Val Glu Pro Tyr Asn Lys Gly Arg Leu Ser Ala Leu Ala Phe Ala
625                 630                 635                 640

Asp Ile Leu Arg Asp Tyr Lys Val Ile Met Ala Glu Asn Ile Pro Glu
```

645                         650                              655

Asn  Pro  Leu  Lys  Tyr  Leu  Tyr  Pro  Asp  Ile  Pro  Lys  Asp  Lys  Ala  Phe
               660                        665                      670

Gly  Lys  His  Tyr  Ser  Ser  Gln  Pro  Cys  Glu  Val  Ser  Arg  Pro  Thr  Glu
               675                        680                      685

Arg  Gly  Asp  Lys  Gly  Tyr  Val  Pro  Ser  Val  Phe  Ile  Pro  Ile  Ser  Thr
     690                        695                      700

Ile  Arg  Ser  Asp  Ser  Thr  Glu  Pro  Gln  Ser  Pro  Ser  Asp  Leu  Leu  Pro
705                      710                       715                       720

Met  Ser  Pro  Ser  Ala  Tyr  Ala  Val  Leu  Arg  Glu  Asn  Leu  Ser  Pro  Thr
                    725                        730                      735

Thr  Ile  Glu  Thr  Ala  Met  Asn  Ser  Pro  Tyr  Ser  Ala  Glu
               740                        745

( 2 ) INFORMATION FOR SEQ ID NO:16:

( i ) SEQUENCE CHARACTERISTICS:
        ( A ) LENGTH: 734 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

Met  Ala  Gly  Trp  Ile  Gln  Ala  Gln  Gln  Leu  Gln  Gly  Asp  Ala  Leu  Arg
1                   5                         10                       15

Gln  Met  Gln  Val  Leu  Tyr  Gly  Gln  His  Phe  Pro  Ile  Glu  Val  Arg  His
               20                        25                       30

Tyr  Leu  Ala  Gln  Trp  Ile  Glu  Ser  Gln  Pro  Trp  Asp  Ala  Ile  Asp  Leu
          35                        40                       45

Asp  Asn  Pro  Gln  Asp  Arg  Ala  Gln  Val  Thr  Gln  Leu  Leu  Glu  Gly  Leu
     50                        55                       60

Val  Gln  Glu  Leu  Gln  Lys  Lys  Ala  Glu  His  Gln  Val  Gly  Glu  Asp  Gly
65                       70                       75                       80

Phe  Leu  Leu  Lys  Ile  Lys  Leu  Gly  His  Tyr  Val  His  Val  Ser  Ser  Arg
                    85                        90                       95

Thr  Arg  Thr  Thr  Ala  Ala  Pro  Trp  Ser  Trp  Leu  Arg  Cys  Ile  Arg  His
               100                       105                      110

Ile  Leu  Tyr  Asn  Glu  Gln  Arg  Leu  Val  Arg  Glu  Ala  Thr  Asn  Gly  Asn
          115                       120                      125

Ser  Ser  Ala  Gly  Ile  Leu  Val  Asp  Ala  Met  Ser  Gln  Lys  His  Leu  Gln
     130                       135                      140

Ile  Asn  Gln  Thr  Phe  Glu  Glu  Leu  Arg  Leu  Val  Thr  Gln  Asp  Thr  Glu
145                      150                       155                      160

Asn  Glu  Leu  Lys  Lys  Leu  Gln  Gln  Thr  Gln  Glu  Tyr  Phe  Ile  Ile  Gln
                    165                       170                      175

Tyr  Gln  Glu  Ser  Leu  Arg  Ile  Gln  Ala  Gln  Phe  Ala  Gln  Leu  Ala  Gln
               180                       185                      190

Leu  Asn  Pro  Gln  Glu  Arg  Leu  Ser  Arg  Glu  Thr  Ala  Leu  Gln  Gln  Lys
          195                       200                      205

Gln  Val  Ser  Leu  Glu  Ala  Trp  Leu  Gln  Arg  Glu  Ala  Gln  Thr  Leu  Gln
     210                       215                      220

Gln  Tyr  Arg  Val  Glu  Leu  Ala  Glu  Lys  His  Gln  Lys  Thr  Leu  Gln  Leu
225                      230                       235                      240

Leu  Arg  Lys  Gln  Gln  Thr  Ile  Ile  Leu  Asp  Asp  Glu  Leu  Ile  Gln  Trp
                    245                       250                      255

| | | | | | | | | | | | | | | |
|---|---|---|---|---|---|---|---|---|---|---|---|---|---|---|
| Lys | Arg | Arg | His<br>260 | Asp | Trp | Arg | Gly | Met<br>265 | Glu | Ala | Pro | Pro | Arg<br>270 | Ser | Leu |
| Asp | Val | Leu | Gln<br>275 | Ser | Trp | Cys | Glu<br>280 | Lys | Leu | Ala | Glu | Ile<br>285 | Ile | Trp | Gln |
| Asn | Arg<br>290 | Gln | Gln | Ile | Arg<br>295 | Arg | Ala | Glu | His | Leu<br>300 | Cys | Gln | Gln | Leu | Pro |
| Ile<br>305 | Pro | Gly | Pro | Val<br>310 | Glu | Glu | Met | Leu | Ala<br>315 | Glu | Val | Asn | Ala | Thr | Ile<br>320 |
| Thr | Asp | Ile | Ile | Ser<br>325 | Ala | Leu | Val | Thr | Ser<br>330 | Thr | Phe | Ile | Ile | Glu<br>335 | Lys |
| Gln | Pro | Pro | Gln<br>340 | Val | Leu | Lys | Thr<br>345 | Gln | Thr | Lys | Phe | Ala<br>350 | Ala | Thr | Val |
| Arg | Leu | Leu<br>355 | Val | Gly | Gly | Lys | Leu<br>360 | Asn | Val | His | Met | Asn<br>365 | Pro | Pro | Gln |
| Val | Lys<br>370 | Ala | Thr | Ile | Ile | Ser<br>375 | Glu | Gln | Gln | Ala | Lys<br>380 | Ser | Leu | Leu | Lys |
| Asn<br>385 | Glu | Asn | Thr | Arg | Asn<br>390 | Glu | Cys | Ser | Gly | Glu<br>395 | Ile | Leu | Asn | Asn | Cys<br>400 |
| Cys | Val | Met | Glu | Tyr<br>405 | His | Gln | Arg | Thr | Gly<br>410 | Thr | Leu | Ser | Ala | His<br>415 | Phe |
| Arg | Asn | Met | Ser<br>420 | Leu | Lys | Arg | Ile | Lys<br>425 | Arg | Ala | Asp | Arg | Arg<br>430 | Gly | Ala |
| Glu | Ser | Val<br>435 | Thr | Glu | Glu | Lys | Phe<br>440 | Thr | Val | Leu | Phe | Glu<br>445 | Ser | Gln | Phe |
| Ser | Val<br>450 | Gly | Ser | Asn | Glu | Leu<br>455 | Val | Phe | Gln | Val | Lys<br>460 | Thr | Leu | Ser | Leu |
| Pro<br>465 | Val | Val | Val | Ile<br>470 | Val | His | Gly | Ser | Gln<br>475 | Asp | His | Asn | Ala | Thr | Ala<br>480 |
| Thr | Val | Leu | Trp | Asp<br>485 | Asn | Ala | Phe | Ala | Glu<br>490 | Pro | Gly | Arg | Val | Pro<br>495 | Phe |
| Ala | Val | Pro | Asp<br>500 | Lys | Val | Leu | Trp | Pro<br>505 | Gln | Leu | Cys | Glu | Ala<br>510 | Leu | Asn |
| Met | Lys | Phe<br>515 | Lys | Ala | Glu | Val | Gln<br>520 | Ser | Asn | Arg | Gly | Leu<br>525 | Thr | Lys | Glu |
| Asn | Leu<br>530 | Leu | Phe | Leu | Ala | Gln<br>535 | Lys | Leu | Phe | Asn | Ser<br>540 | Ser | Ser | His | |
| Leu<br>545 | Glu | Asp | Tyr | Asn | Gly<br>550 | Met | Ser | Val | Ser | Trp<br>555 | Ser | Gln | Phe | Asn | Arg<br>560 |
| Glu | Asn | Leu | Pro | Gly<br>565 | Trp | Asn | Tyr | Thr | Phe<br>570 | Trp | Gln | Trp | Phe | Asp<br>575 | Gly |
| Val | Met | Glu | Val<br>580 | Leu | Lys | Lys | His | His<br>585 | Lys | Pro | His | Trp | Asn<br>590 | Asp | Gly |
| Ala | Ile | Leu<br>595 | Gly | Phe | Val | Asn | Lys<br>600 | Gln | Gln | Ala | His | Asp<br>605 | Leu | Leu | Ile |
| Asn | Lys<br>610 | Pro | Asp | Gly | Thr | Phe<br>615 | Leu | Leu | Arg | Phe | Ser<br>620 | Asp | Ser | Glu | Ile |
| Gly<br>625 | Gly | Ile | Thr | Ile | Ala<br>630 | Trp | Lys | Phe | Asp | Ser<br>635 | Pro | Asp | Arg | Asn | Leu<br>640 |
| Trp | Asn | Leu | Lys | Pro<br>645 | Phe | Thr | Thr | Arg | Glu<br>650 | Gly | Ser | Ile | Arg | Ser<br>655 | Leu |
| Ala | Asp | Arg | Leu<br>660 | Gly | Asp | Leu | Asn | Tyr<br>665 | Leu | Ile | Tyr | Val | Phe<br>670 | Pro | Asp |
| Arg | Pro | Lys | Asp | Glu | Val | Phe | Ser | Lys | Tyr | Tyr | Thr | Pro | Val | Leu | Ala |

|     |     |     |     | 675 |     |     |     |     | 680 |     |     |     |     | 685 |     |
| --- | --- | --- | --- | --- | --- | --- | --- | --- | --- | --- | --- | --- | --- | --- | --- |
| Lys | Ala | Val | Asp | Gly | Tyr | Val | Lys | Pro | Gln | Ile | Lys | Gln | Val | Val | Pro |
|     | 690 |     |     |     | 695 |     |     |     |     | 700 |     |     |     |     |     |
| Glu | Phe | Val | Ser | Ala | Ser | Ala | Asp | Ser | Ala | Gly | Ser | Arg | His | Leu | His |
| 705 |     |     |     |     | 710 |     |     |     |     | 715 |     |     |     |     | 720 |
| Gly | Pro | Gly | Ser | Leu | Pro | Ser | Arg | Val | Pro | Pro | Ala | Ser | Leu |     |     |
|     |     |     |     | 725 |     |     |     |     | 730 |     |     |     |     |     |     |

(2) INFORMATION FOR SEQ ID NO:17:

(i) SEQUENCE CHARACTERISTICS:
(A) LENGTH: 263 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:17:

| Met | Gln | Trp | Gln | Gln | Leu | Leu | Gln | Gln | Leu | Tyr | Asp | Phe | Pro | Glu | Arg |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Leu | Ala | Trp | Ile | Glu | Gln | Trp | Ala | Ala | Thr | Leu | Leu | Leu | Leu | Arg | Glu |
|     |     |     | 20  |     |     |     |     | 25  |     |     |     |     | 30  |     |     |
| Leu | His | Asn | Gln | Pro | Ile | Leu | Glu | Glu | Arg | Leu | Ala | Gln | Gln | Lys | Gln |
|     |     |     | 35  |     |     |     |     | 40  |     |     |     |     | 45  |     |     |
| Asp | Lys | Leu | Leu | Asp | Arg | Glu | Leu | Leu | Glu | Leu | Trp | Lys | Arg | Arg | Gln |
|     | 50  |     |     |     |     | 55  |     |     |     |     | 60  |     |     |     |     |
| Gln | Ala | Cys | Ile | Gly | Pro | Leu | Asp | Leu | Gln | Leu | Ala | Leu | Tyr | Asp | Pro |
| 65  |     |     |     |     | 70  |     |     |     |     | 75  |     |     |     |     | 80  |
| Leu | Arg | Leu | Leu | Ser | Phe | Val | Val | Glu | Gln | Pro | Cys | Met | Pro | Pro | Arg |
|     |     |     |     | 85  |     |     |     |     | 90  |     |     |     |     | 95  |     |
| Pro | Lys | Thr | Gly | Val | Phe | Thr | Val | Arg | Leu | Leu | Glu | Asn | Lys | Asp | Lys |
|     |     |     | 100 |     |     |     |     | 105 |     |     |     |     | 110 |     |     |
| Leu | Gly | Arg | Phe | Asn | Lys | Glu | Leu | Phe | His | Leu | Glu | Lys | Val | Thr | Glu |
|     |     |     | 115 |     |     |     |     | 120 |     |     |     |     | 125 |     |     |
| Glu | Leu | His | Phe | Gly | Leu | Ile | Leu | Thr | Ser | Leu | Pro | Val | Val | Val | Ile |
|     | 130 |     |     |     |     | 135 |     |     |     |     | 140 |     |     |     |     |
| Ser | Asn | Gln | Asn | Ala | Trp | Ala | Ser | Ile | Leu | Trp | Asn | Asn | Phe | Phe | Pro |
| 145 |     |     |     |     | 150 |     |     |     |     | 155 |     |     |     |     | 160 |
| Pro | Trp | Gln | Leu | Glu | Leu | Ser | Trp | Gln | Phe | Ser | Ser | Val | Arg | Gly | Leu |
|     |     |     |     | 165 |     |     |     |     | 170 |     |     |     |     | 175 |     |
| Glu | Gln | Leu | Leu | Ala | Lys | Leu | Trp | Phe | Lys | Glu | Gly | Phe | Phe | Trp | Trp |
|     |     |     | 180 |     |     |     |     | 185 |     |     |     |     | 190 |     |     |
| Asp | Ile | Leu | Leu | Lys | Lys | His | Leu | Trp | Asn | Asp | Gly | Ile | Met | Gly | Pro |
|     |     |     | 195 |     |     |     |     | 200 |     |     |     |     | 205 |     |     |
| Ser | Lys | Glu | Arg | Leu | Leu | Gly | Thr | Phe | Leu | Leu | Arg | Phe | Ser | Glu | Ser |
|     | 210 |     |     |     |     | 215 |     |     |     |     | 220 |     |     |     |     |
| Gly | Gly | Ile | Thr | Trp | Val | Val | Pro | Tyr | Thr | Lys | Leu | Ser | Asp | Ile | Ile |
| 225 |     |     |     |     | 230 |     |     |     |     | 235 |     |     |     |     | 240 |
| Arg | Tyr | Asn | Ile | Pro | Pro | Leu | Leu | Tyr | Pro | Ile | Lys | Ala | Phe | Gly | Lys |
|     |     |     |     | 245 |     |     |     |     | 250 |     |     |     |     | 255 |     |
| Glu | Glu | Leu | Pro | Leu | Pro | Ser |     |     |     |     |     |     |     |     |     |
|     |     |     | 260 |     |     |     |     |     |     |     |     |     |     |     |     |

INTERLEUKIN 4 SIGNAL TRANSDUCERS

CROSS-REFERENCE TO RELATED APPLICATIONS;

This application is a continuation-in-part of application Ser. No. 08/269,604 entitled "Interleukin 4 Signal Transducers and Binding Assays" and filed Jul. 5, 1994, abandoned, the disclosure of which is hereby incorporated by reference.

INTRODUCTION

1. Field of the Invention

The field of this invention is interleukin 4 signal transducers.

2. Background

Identifying and developing new pharmaceuticals is a multibillion dollar industry in the U.S. alone. Gene specific transcription factors provide a promising class of targets for novel therapeutics directed to these and other human diseases. Urgently needed are efficient methods of identifying pharmacological agents or drugs which are active at the level of gene transcription. If amenable to automated, cost-effective, high throughput drug screening, such methods would have immediate application in a broad range of domestic and international pharmaceutical and biotechnology drug development programs.

Immunosuppression is therapeutically desirable in a wide variety of circumstances including transplantation, allergy and other forms of hypersensitivity, autoimmunity, etc. Cyclosporin, a widely used drug for effecting immunosuppression, is believed to act by inhibiting a calcineurin, a phosphatase which activates certain transcription factors. However, because of side effects and toxicity, clinical indications of cyclosporin (and the more recently developed FK506) are limited.

Interleukin-4 (IL-4) is an immunomodulatory cytokine secreted by activated T lymphocytes, basophils and mast cells. IL-4 plays an important role in modulating the balance of T helper cell subsets, favoring expansion of the Th2 lineage relative to Th1. Imbalance of these T lymphocyte subsets has been implicated in immunological diseases including allergy, inflammation and autoimmune disease. Accordingly, it is desired to identify agents which specifically interfere with transduction of IL-4 signalling. Unfortunately, the reagents necessary for the development of high-throughput screening assays for such therapeutics are unavailable.

3. Relevant Literature

For recent reviews, see W. E. Paul and R. A. Seder (1994) Cell 76, 241–251 and Darnell et al. (1994) Science 264, 1415. More specific references include: Shuai et at. (1992) Science 258, 1808–1812; Kotanides and Reich (1993) Science 262, 1265–1267; Schindler et al. (1994) The EMBO J 13, 1350–1356; Ingrid Kohler and E. P. Rieber (1993) Eur J Immunol 23, 3066–3071. For recent work relating to the IFN-g receptor and p91, see Shuai et at., (1994) and Greenlund et at., (1994) The EMBO I 13, 4604–4610. See also copending U.S. applications Ser. Nos. 08/246,977 and 08/046,585.

SUMMARY OF THE INVENTION

The invention provides methods and compositions for identifying pharmacological agents useful in the diagnosis or treatment of disease associated with the expression of one or more genes modulated by a transcription complex containing an interleukin signal transducer and activator of transcription, IL-4 Stat. The invention also provides methods and composition useful in diagnosis and therapy for disease associated with undesirable cell growth, differentiation and/or cytokine signal responsiveness.

The invention provides recombinant human IL-4 Stat peptides capable of selectively binding binding targets of IL-4 Stat. Such binding targets are or derive from natural intracellular binding targets and include transcription factors, enzymes such as a phosphatases or kinases, cellular receptors such as the IL-4 receptor and nucleic acids, such as nucleic acids encoding one or more IL-4 Stat binding sequences. Nucleic acid encoding the subject IL-4 Stat portions, vectors and cells comprising such nucleic acids are used to as probes for IL-4 Stat homologs and/or for recombinantly producing IL-4 Stat peptides. The invention also provides IL-4 Stat binding targets such as cytokine receptor peptides; in particular, IL-4 receptor peptides which selectively bind IL-4 Stat peptides, nucleic acids encoding such receptor peptides, and binding reagents, such as antibodies selective for such peptides or for IL-4 Stat peptides.

In one embodiment, the invention provides methods of identifying a pharmacological agent useful in the diagnosis or treatment of disease associated with the expression of an IL-4 Stat-modulated gene. In general, the methods involve combining a IL-4 Stat peptide capable of selectively binding a natural cellular binding target of the IL-4 Stat with at least a portion, fragment or structural analog of a natural cellular target of the IL-4 Stat that is sufficient to selectively bind the IL-4 Stat, and a candidate pharmacological agent. The resultant mixture is incubated under conditions whereby, but for the presence of the candidate pharmacological agent, the IL-4 Stat peptide selectively binds the binding target. Then the presence or absence of selective binding between the IL-4 Stat peptide and the binding target is detected; where the absence of selective binding indicates that the candidate pharmacological agent is capable of selectively interfering with IL-4 Stat modulated function, such as gene expression. Such an agent is useful in the diagnosis or treatment of disease, particularly immune disease, associated with the expression of the gene.

A wide variety of alternative embodiments of the general methods using IL-4 Stat and IL-4 receptor peptides are disclosed. These encompass a variety of genes, transcription factors and methods for isolating and detecting polypeptides and transcription complexes, e.g. ligand tagging followed by immobilized receptor isolation, direct labels, specific binding labels, etc. The methods are particularly suited to high-throughput screening where one or more steps are performed by a computer controlled electromechanical robot comprising an axial rotatable arm and the solid substrate is a portion of a well of a microtiter plate.

DETAILED DESCRIPTION OF THE INVENTION

The invention provides methods and compositions relating to IL-4 Stats —a novel family of transcription factors. An IL-4 Stat cDNA and amino acid sequence are disclosed in SEQUENCE ID NOS; 1 and 2, respectively. IL-4 Stats are characterized by selective binding to intracellular domains of cytokine receptors and nucleic acids encoding IL-4 Stat binding sites such as shown in Table 1. Preferred binding sites include two trinucleotides of the sequences: TTC and GAA, where the trinucleotides are separated by from 1 to 5 nucleotides. IL-4 Stats include SH2 and SH3 domain structures their amino acid sequences share substantial sequence similarity with that of SEQUENCE ID NOS: 2. Preferred IL-4 Stats have cDNAs which share substantial sequence similarity with that of SEQUENCE ID NO: 1. Polypeptides with substantial sequence similarity present at least about 55%, preferably at least about 70%, more preferably at least about 80%, and most preferably at least about 90% sequence identity as determined by pair-wise distance matrix comparisons carried out using the CLUSTAL V protein alignment software distributed by EMBL. Within the SH2 domain the family members are at least about 65%, preferably at least about 75%, more preferably at least about 85%, most preferably at least about 95% identical as determined by pair-wise distance matrix comparisons. Where the sequences diverge, the differences are preferably conservative, i.e. an acidic for an acidic amino acid substitution.

Substantially identical or homologous nucleic acid sequences hybridize to their respective complements under high stringency conditions, for example, at 55° C. and hybridization buffer comprising 50% formamide in 0.9M saline/0.09M sodium titrate (SSC) buffer and remain bound when subject to washing at 55° C. with the SSC/formamide buffer. Where the sequences diverge, the differences are preferably silent, i.e.or a nucleotide change providing a redundant codon, or conservative, i.e. a nucleotide change providing a conservative amino acid substitution.

The invention provides IL-4 Stat peptides capable of selectively binding at least one natural IL-4 Stat binding target. IL-4 Stat peptides are of length sufficient to provide a novel peptide. As used herein, peptides are at least 5, usually at least about 6, more usually at least about 8, most usually at least about 10 amino acids and up to 50 amino acids in length. Peptides may be present in a free state or bound to other components such as blocking groups to chemically insulate reactive groups (e.g. amines, carboxyls, etc.) of the peptide, fusion peptides or polypeptides (i.e. the peptide may be present as a portion of a larger polypeptide), etc.

The IL-4 Stat peptides are capable of selectively binding at least one natural IL-4 Stat binding target. Exemplary binding targets include cytokine receptors, especially interleukin receptors, especially the IL-4 receptor or receptors with substantial sequence similarity to IL-4 receptors, nucleic acids which comprise one or more IL-4 Stat DNA binding sites, transcription factors including IL-4 Stat itself, etc. Other natural IL-4 Stat binding targets are readily identified by screening cells, membranes and cellular extracts and fractions with the disclosed materials and methods and by other methods known in the art. Binding targets are capable of selectively binding an IL-4 Stat peptide, i.e. with an equilibrium constant at least about $10^4M^{-1}$, preferably at least about $10^6M^{-1}$, more preferably at least about $10^8M^{-1}$ and not less than six, preferably not less than four, more preferably not less than two orders of magnitude less than the binding equilibrium constant of full-length native IL-4 Stat to the binding target under similar conditions.

Preferred peptides include IL-4 Stat amino acid residues sufficient to provide the peptide (or a polypeptide comprising the IL-4 Stat peptide) with binding affinity and specificity similar to that of the native IL-4 Stat. Preferred peptide and target portions capable of imparting the requisite binding specificity and affinity are readily identified by those skilled in the art. A wide variety of molecular and biochemical methods are available for generating preferred portions, see e.g. Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, NY, N.Y., 1992) or that are otherwise known in the art. For example, deletion mutants are screened for selective protein or sequence-specific binding directly using binding assays including those described herein or other assays such as fluorescence resonance energy transfer (FRET) or electrophoretic mobility shift analysis (EMSA).

Also provided are novel agents which selectively bind the subject IL-4 Stat peptides. Included are novel portions of natural cellular binding targets and antibodies. Excluded are natural and known products such as the published full-length IL-4 receptor. However, cytokine receptors, particularly interleukin receptors, particularly the IL-4 receptor is shown herein to contain peptides which selectively bind IL-4 Stat. Thus, the invention provides novel peptides of known proteins (e.g. IL-4 receptor peptides) flanked by other than a naturally flanking amino acid residue. Hence, the peptides may be flanked on one or both sides by one or more amino acid residues not naturally flanking the peptide in the native state or the peptides may terminate in an amino acid residue without a distal peptide bond, i.e. at least one of an N or C terminal residue with not joined to another amino acid. Materials and methods for making such agents (e.g. nucleic acids encoding the IL-4 receptor peptides) are disclosed herein or otherwise known in the art. Methods for making IL-4 Stat peptide- and IL-4 receptor peptide-specific antibodies, including monoclonals, are described in Harlow and Lane, Antibodies: A laboratory Manual, Cold Spring Harbor, 1988.

The invention provides efficient methods of identifying pharmacological agents or drugs which are active at the level of IL-4 Stat and IL-4 receptor modulatable cellular function, particularly gene transcription. The methods are amenable to automated, cost-effective high throughput drug screening and have immediate application in a broad range of domestic and international pharmaceutical and biotechnology drug development programs.

Target therapeutic indications are limited only in that the target cellular function (e.g. gene expression) be subject to inhibition by alteration of the formation of a complex (e.g. transcription complex) comprising the subject IL-4 Stat or IL-4 receptor and/or its specific interaction natural cellular binding targets (e.g.with a gene or gene regulatory region). Since a wide variety of genes are subject to IL-4 Stat or IL-4 receptor-modulated gene transcription, target indications may include viral, bacterial and fungal infections, metabolic disease, genetic disease, cell growth and regulatory disfunction, such as neoplasia, inflammation, hypersensitivity, etc. Frequently, the target indication is an undesirable immune response, for example, in transplantation and transfusion, all types of hypersensitivity including immediate types such as allergies and delayed types, autoimmunity including that induced by viral infection such as HIV.

The invention provides a wide variety of binding and expression assays for compounds which interfere with IL-4 receptor or IL-4 Stat modulated gene transcription. While the following descriptions are directed primarily to IL-4 Stat assays, they are also analogously applicable to IL-4 receptor peptide based assays. The disruption of IL-4 Stat binding may be detected with a IL-4 Stat peptide (or peptide containing polypeptide) and an IL-4 receptor peptide which binds IL-4 Stat. Either component may be labelled, e.g. with radiolabelled phosphate using HMK and either component may be immobilized, eg. by labeling with biotin and binding to an avidin coated substrate. Alternatively, the disruption of IL-4 Stat-IL-4 Stat dimerization or IL-4 Stat—DNA binding may be assayed. IL-4 Stat peptides may be obtained by any convenient way, for example, by chemical synthesis, expression in vaccinia or baculovirus-based expression systems, etc. To obtain active, tyrosine phosphorylated IL-4 Stat, IL-4 Stat can be coexpressed with a JAK kinase. Alternatively, recombinant IL-4 Stat can be treated with an exogenous IL-4 Stat kinase in the form of cellular extracts or purified preparations thereof.

Peptides (or polypeptides containing such peptides) used in the disclosed methods are usually added in an isolated, partially pure or pure form and are typically recombinantly produced. As used herein, an "isolated" peptide is unaccompanied by at least some of the material with which it is associated in its natural state and constitutes at least about 0.5%, preferably at least about 2%, and more preferably at least about 5% by weight of the total protein (including peptide) in a given sample; a partially pure peptide constitutes at least about 10%, preferably at least about 30%, and more preferably at least about 60% by weight of the total protein in a given sample; and a pure peptide constitutes at least about 70%, preferably at least about 90%, and more preferably at least about 95% by weight of the total protein in a given sample. It is often desirable that the peptide be part of a fusion product with another peptide or polypeptide, e.g. a polypeptide that is capable of providing or enhancing protein-protein binding, sequence-specific nucleic acid binding or stability under assay conditions (e.g. a tag for detection or anchoring).

The assay mixtures comprise at least a portion of a natural cellular IL-4 Stat binding target such as an IL-4 receptor peptide or a nucleic acid comprising a sequence which shares sufficient sequence similarity with a gene or gene regulatory region to which the native IL-4 Stat naturally binds to provide sequence-specific binding of the IL-4 Stat peptide (or peptide-containing polypeptide). The nucleic acid may further comprise one or more sequences which facilitate the binding of a second transcription factor peptide (or peptide containing polypeptide) which cooperatively binds the nucleic acid with the IL-4 Stat peptide (i.e. at least one increases the affinity or specificity of the DNA binding of the other). While native binding targets may be used, it is frequently preferred to use portions (e.g. peptides, nucleic acid fragments) or analogs (i.e. agents which mimic the IL-4 binding properties of the natural binding target for the purposes of the assay) thereof so long as the portion provides binding affinity and avidity to the IL-4 Stat peptide conveniently measurable in the assay.

Binding site portions of the nucleic acid constitute at least about 4, preferably at least about 6, more preferably at least about 8 nucleotides. Nucleic acids comprising an IL-4 Stat binding site include at least a portion of a nucleotide sequence in Table 1, preferably including the sequence TTC–GAA on one strand where TTC and GAA are separated by from 1 to 5 nucleotides.

TABLE 1

| | | | |
|---|---|---|---|
| FcγRI | 5'-GTATTTCCCAGAAAAGGAAC →<br>CATAAAGGGTCTTTTCCTTG ← | (SEQ ID NO: 03) | −33/−14 |
| FcεRIIa | -CTCTTACCTGAGAAATGG →<br>← | (SEQ ID NO: 04) | −131/−114 |
| FcεRIIb | -GAATTCTAAGAAAGGG →<br>← | (SEQ ID NO: 05) | −230/−214 |
| $C_\gamma 1$ | -ACATCACATGAAGTA →<br>← | (SEQ ID NO: 06) | −126/−111 |
| $C_\epsilon$ | -AACTTCCCAAGAACAG →<br>← | (SEQ ID NO: 07) | −119/−104 |
| mMHCIIEβ | -AAGGTTTCAGAAGGG →<br>← | (SEQ ID NO: 08) | −165/−152 |
| hMHCIIDRα | -CCTTCCCCTAGCAACAG →<br>← | (SEQ ID NO: 09) | −115/−99 |

Binding sequences for other transcription factors may be found in sources such as the Transcription Factor Database of the National Center for Biotechnology Information at the National Library for Medicine, in Faisst and Meyer (1991) Nucleic Acids Research 20, 3–26, and others known to those skilled in this art.

The nucleic acid portion bound by the peptide(s) may be continuous or segmented. Additional nucleotides may used to provide structure which enhances or decreased binding or stability, etc. For example, combinatorial DNA binding can be effected by including two or more DNA binding sites for different or the same transcription factor on the oligonucleotide. This allows for the study of cooperative or synergistic DNA binding of two or more factors. In addition, the nucleic acid can comprise a cassette into which transcription factor binding sites are conveniently spliced for use in the subject assays.

The nucleic acid is usually linear and double-stranded DNA, though circular plasmids or other nucleic acids or structural analogs may be substituted so long as IL-4 Stat sequence-specific binding is retained. In some applications, supercoiled DNA provides optimal sequence-specific binding and is preferred. The nucleic acid is often recombinant, meaning it comprises a sequence joined to a nucleotide other than that which it is joined to on a natural chromosome. An isolated nucleic acid constitutes at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction. The nucleic acid may be of any length amenable to the assay conditions and requirements. Typically the nucleic acid is between 8 bp and 5 kb, preferably between about 12 bp and 1 kb, more preferably between about 18 bp and 250 bp, most preferably between about 27 and 50 bp.

The assay mixture also comprises a candidate pharmacological agent. Candidate agents encompass numerous chemical classes, though typically they are organic compounds; preferably small organic compounds. Small organic compounds have a molecular weight of more than 50 yet less than about 2,500, preferably less than about 1000, more preferably, less than about 500. Candidate agents comprise functional chemical groups necessary for structural interactions with proteins and/or DNA, and typically include at least an amine, carbonyl, hydroxyl or carboxyl group, preferably at least two of the functional chemical groups, more preferably at least three. The candidate agents often comprise cyclical carbon or heterocyclic structures and/or aromatic or polyaromatic structures substituted with one or more of the forementioned functional groups. Candidate agents are also found among biomolecules including peptides, saccharides, fatty acids, steroids, purines, pyrimidines, derivatives, structural analogs or combinations thereof, and the like.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs.

A variety of other reagents may also be included in the mixture. These include reagents like salts, buffers, neutral proteins, e.g. albumin, detergents, etc. which may be used to facilitate optimal protein-protein and/or protein-nucleic acid binding and/or reduce non-specific or background interactions, etc. Also, reagents that otherwise improve the efficiency of the assay, such as protease inhibitors, nuclease inhibitors, antimicrobial agents, etc. may be used.

The resultant mixture is incubated under conditions whereby, but for the presence of the candidate pharmacological agent, the IL-4 Stat peptide (or IL-4 Stat peptide containing polypeptide) selectively binds the cellular binding target, portion or analog. The mixture components can be added in any order that provides for the requisite bindings. Incubations may be performed at any temperature which facilitates optimal binding, typically between 4° and 40° C., more commonly between 15° and 40° C. Incubation periods are likewise selected for optimal binding but also minimized to facilitate rapid, high-throughput screening, and are typically between. 1 and 10 hours, preferably less than 5 hours, more preferably less than 2 hours.

After incubation, the presence or absence of selective binding between the IL-4 Stat peptide and one or more binding targets is detected by any convenient way. Often, a separation step is used to separate bound from unbound components. The separation step may be accomplished in a variety of ways. Conveniently, at least one of the components is immobilized on a solid substrate which may be any solid from which the unbound components may be conveniently separated. The solid substrate may be made of a wide variety of materials and in a wide variety of shapes, e.g. microtiter plate, microbead, dipstick, resin particle, etc. The substrate is chosen to maximize signal to noise ratios, primarily to minimize background binding, for ease of washing and cost.

Separation may be effected for example, by removing a bead or dipstick from a reservoir, emptying or diluting reservoir such as a microtiter plate well, rinsing a bead (e.g. beads with iron cores may be readily isolated and washed using magnets), particle, chromatographic column or filter with a wash solution or solvent. Typically, the separation step will include an extended rinse or wash or a plurality of rinses or washes. For example, where the solid substrate is a microtiter plate, the wells may be washed several times with a washing solution, which typically includes those components of the incubation mixture that do not participate in specific binding such as salts, buffer, detergent, nonspecific protein, etc. may exploit a polypeptide specific binding reagent such as an antibody or receptor specific to a ligand of the polypeptide.

Detection may be effected in any convenient way. Frequently, one of the components comprises or is coupled to a label. A wide variety of labels may be employed— essentially any label that provides for detection of bound protein. The label may provide for direct detection as radioactivity, luminescence, optical or electron density, etc. or indirect detection such as an epitope tag, an enzyme, etc. The label may be appended to the protein e.g. a phosphate group comprising a radioactive isotope of phosphorous, or incorporated into the protein structure, e.g. a methionine residue comprising a radioactive isotope of sulfur.

A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters. Candidate agents shown to inhibit IL-4 peptide —target binding or transcription complex formation provide valuable reagents to the pharmaceutical industries for animal and human trials.

The methods are particularly suited to automated high throughput drug screening. In a preferred embodiment, the individual sample incubation volumes are less than about 500 ul, preferably less than about 250 ul, more preferably less than about 100 ul. Such small sample volumes minimize the use of often scarce candidate agent, expensive transcription complex components, and hazardous radioactive waste. Furthermore, the methods provide for automation, especially computerized automation. Accordingly, the method steps are preferably performed by a computer-controlled electromechanical robot. While individual steps may be separately automated, a preferred embodiment provides a single computer-controlled multifunction robot with a single arm axially rotating to and from a plurality of work stations performing the mixture forming, incubating and separating steps. The computer is loaded with software which provides the instructions which direct the arm and work station operations and provides input (e.g. keyboard and/or mouse) and display (e.g. monitor) means for operator interfacing.

In another embodiment, the methods involve combining the first IL-4 Stat peptide (or peptide-containing polypeptide), a labelled form of an IL-4 Stat peptide binding target (e.g. a different transcription factor peptide (or peptide containing polypeptide)), the candidate pharmacological agent, a receptor immobilized on a solid substrate and the nucleic acid conjugated to a ligand capable of specifically binding the receptor.

The labelled target comprises a label that provides for detection of the labelled target when complexed, directly or indirectly, to the nucleic acid conjugate. The nucleic acid conjugate comprises an IL-4 Stat binding sequence, as previously described, coupled to a ligand. The ligand of the nucleic acid conjugate is capable of specifically binding the immobilized receptor. The ligand-receptor binding is specific enough to provide a maximized and at least measurable signal to noise ratio (receptor mediated vs. non-specific retention of the label on the substrate). The nucleic acid conjugate is typically capable of binding the receptor with an affinity of at least about $10^5 M^{-1}$, preferably at least about $10^6 M^{-1}$, more preferably at least about $10^8 M^{-1}$. In a preferred embodiment, a plurality of ligands are capable of binding each receptor. Exemplary ligand-receptor pairs include biotin and avidin, antigen and antibody, sugar and lectin, ion and chelator, etc.

As above, the mixture usually includes additional reagents to facilitate optimal receptor-ligand and protein-nucleic acid binding or to reduce non-specific or background protein-substrate, nucleic acid-substrate, protein-protein and protein-DNA interactions, etc. The mixture is incubated under conditions whereby the receptor is bound to the ligand anti, but for the presence of the candidate pharmacological agent, the IL-4 Stat peptide is sequence-specifically bound to the nucleic acid conjugate and the labelled target is selectively bound to the IL-4 Stat peptide. Incubations are as previously described. After receptor-ligand and protein-nucleic acid binding have occurred, a fraction comprising labelled target which is not directly or sequence-specifically bound through the IL-4 Stat peptide is separated from the solid substrate. This step may be accomplished in a variety of ways as described above. After separating the unbound fraction from the solid substrate, the presence of bound nucleic acid-protein complex is detected via the labeled target.

As previously described, the methods are particularly suited to automated high throughput drug screening. In a particular embodiment, the arm retrieves and transfers a microtiter plate to a liquid dispensing station where measured aliquots of each an incubation buffer and a solution comprising one or more candidate agents are deposited into each designated well. The arm then retrieves and transfers to and deposits in designated wells a measured aliquot of a solution comprising a labeled transcription factor protein. After a first incubation period, the liquid dispensing station deposits in each designated well a measured aliquot of a biotinylated nucleic acid solution. The first and/or following second incubation may optionally occur after the arm transfers the plate to a shaker station. After a second incubation period, the arm transfers the microtiter plate to a wash station where the unbound contents of each well is aspirated and then the well repeatedly filled with a wash buffer and aspirated. Where the bound label is radioactive phosphorous, the arm retrieves and transfers the plate to the liquid dispensing station where a measured aliquot of a scintillation cocktail is deposited in each designated well. Thereafter, the amount of label retained in each designated well is quantified.

In more preferred embodiments, the liquid dispensing station and arm are capable of depositing aliquots in at least eight wells simultaneously and the wash station is capable of filling and aspirating ninety-six wells simultaneously. Preferred robots are capable of processing at least 640 and preferably at least about 1,280 candidate agents every 24 hours, e.g. in microtiter plates. Of course, useful agents are identified with a range of other assays (e.g. gel shifts, etc.) employing IL-4 Stat- peptides.

IL-4 Stat peptides and nucleic acids provide a wide variety of uses in addition to the in vitro binding assays described above. For example, cell-based assays are provided which involve transfecting an IL-4 receptor peptide (or peptide containing polypeptide, e.g. full length receptor) expressing cell such as ThP1 with an IL-4 Stat inducible reporter such as luciferase. Agents which modulate IL-4 Stat mediated cell function are then detected through a change in the reporter. Another approach is a transient expression assay. In this method, cells are transfected with one or more constructs encoding in sum, a polypeptide comprising a portion of IL-4 Stat capable of selectively binding an natural IL-4 target and a reporter under the transcriptional control of a promoter comprising a functional IL-4 Stat binding site. The cell may advantageously also be cotransfected with a construct encoding an IL-4 Stat activator, usually a tyrosine kinase, particularly a Jak kinase.

The subject peptides provide useful lead compounds for designing structural analogs for use in binding assays and therapy (below). Additionally, the subject nucleic acids find use as hybridization probes for identifying IL-4 Stat cDNA homologs with substantial sequence similarity. Given the subject probes, materials and methods for probing cDNA and genetic libraries and recovering homologs are known in the art. Preferred libraries are derived from human immune cells, tumor cells, and neural cells; more preferred are cDNA libraries from differentiated human lymphoid cells. These IL-4 Stat cDNA homologs in turn provide additional Stat peptides for use in binding assays and therapy as described herein.

The subject compositions also provide therapeutic applications. For example, IL-4 Stat peptides or IL-4 receptor peptides such as the inhibitory peptides NH$_2$-GP-PGEAGYKAFSSLL(SEQ ID NO:10)-COOH and NH$_2$-ASSGEEGYKPFQDLI(SEQ ID NO:11)-COOH, and phosphotyrosine containing portions thereof, find use in treating disease associated with undesirable cell growth, differentiation, particularly immune cell differentiation, and cytokine, particularly interleukin, more particularly IL-4, responsiveness. For therapeutic uses, the compositions and agents disclosed herein may be administered by any convenient way, preferably parenterally, conveniently in a physiologically acceptable carrier, e.g., phosphate buffered saline, saline, deionized water, or the like. Typically, the compositions are added to a retained physiological fluid such as blood or synovial fluid. Generally, the amount administered will be empirically determined, typically in the range of about 10 to 1000 μg/kg of the recipient. For peptide agents, the concentration of will generally be in the range of about 100 to 500 μg/ml in the dose administered. Other additives may be included, such as stabilizers, bactericides, etc. These additives will be present in conventional amounts.

IL-4 Stat peptide-and IL-4 receptor-encoding nucleic acids find use in therapeutic gene therapy. For example, such nucleic acids are cloned into a virus and the virus used to transfect and confer cytokine responsiveness to tumor cells. For gene therapy involving the transfusion of IL-4 Stat transfected cells, administration will depend on a number of variables that are ascertained empirically. For example, the number of cells will vary depending on the stability of the transfused cells. Transfusion media is typically a buffered saline solution or other pharmacologically acceptable solution. Similarly the amount of other administered compositions, e.g. transfected nucleic acid, protein, etc., will depend on the manner of administration, purpose of the therapy, and the like.

EXPERIMENTAL

Interleukin-4 (IL-4), like IFN-g, rapidly alters the pattern of gene expression in cells beating its cognate receptor. B lymphocytes, when exposed to IL-4, activate the synthesis of sterile transcripts of the immunoglobulin locus and subsequently undergo class switching to the IgE heavy chain isotype (Coffman et al., 1993). IL-4 also activates genes encoding cell surface proteins including various immunoglobulin receptors and the MHC class II antigen (Noelle et al., 1984: Roehm et at., 1984; Defrance et al., 1987; Hudak et al., 1987; Conrad et al., 1987). Like with IFN-g, a latent DNA binding protein is rapidly phosphorylated on tyrosine and translocated to the nucleus in receptor-bearing cells treated with IL-4 (Kohler and Rieber, 1993; Kotanides and Reich, 1993; Schindler et al., 1994). We disclose here the purification the IL-4 induced DNA binding protein and the cloning of its encoding gene.

Purification of an IL-4 Induced DNA Binding Protein

Humart monocytic Thp-1 cells were grown in suspension, exposed briefly to IL-4, harvested, disrupted and fractionated to separate nuclear and cytoplasmic proteins. Nuclear extracts prepared from IL-4 treated cells, but not control cells, were observed to contain a DNA binding activity capable of specific interaction with a double stranded, synthetic oligonucleotide corresponding to the IL-4 response element located upstream of the human FcgRI gene (Kotanides and Reich, 1993). This activity was purified by a combination of three chromatographic steps and found to be specified by a polypeptide that migrated with a molecular mass of roughly 100 Kd when sized by denaturing polyacrylamide gel electrophoresis. The 100 Kd polypeptide reacted with an anti-phosphotyrosine antibody, consistent with earlier studies that had implicated tyrosine phosphorylation as an essential step required for its activation (Kotanides and Reich, 1993; Kohler and Rieber, 1993; Schindler et al., 1994).

The purified, 100 Kd polypeptide was digested with lys-C and resulting peptides were fractionated by capillary HPLC. Amino acid sequences were obtained from six peptide fragments. Synthetic oligonucleotides designed from these sequences were used for PCR amplification of cDNA prepared using mRNA from Thp-1 cells. This led to the isolation of a PCR fragment encoding three of the sequenced peptides. cDNA clones were obtained and sequenced, allowing prediction of the open reading frame corresponding to the 100Kd polypeptide. Starting with an initiator methionine codon located 182 base pairs downstream from 5' terminus of the longest cDNA clone, the sequence predicts an open reading frame 848 residues in length. All six of the peptide sequences generated by lys-C digestion of the purified 100Kd polypeptide were found in the conceptually translated open reading frame.

A search of the NCBI BLAST data base revealed substantive similarity between the primary amino acid sequence of the 100 Kd, IL-4 induced protein and that of mammary gland factor (MGF), a prolactin induced DNA binding protein belonging to the Stat family of transcription factors (Wakao et al., 1994). Albeit less striking, sequence similarity was also observed between the IL-4 induced protein and the remaining four members of the Stat family. Table II provides a comparison of the amino acid sequence of the IL-4 induced protein with the sequences of the other known members of the Stat family of transcription factors.

TABLE II

```
                                                   STAT alignment (7/5) Formatted Alignment
IL-4 STAT (7/5)MSLGLVSKM PPE---KVQR IVVD--HPDE RHLRRLQEFR EQPLVGS DAFCCNLASA LLSDTVQHLQ ASVGEQ-GEG STILD-----    79
STAT 5         MAGWIQAQQLQQGDALRQMQV IKQG-HPFLE RRRLVVRFLV EQLQGVGAIDLD NPQDRAQMTQ LLEGLMQELQ KKAEHQVGKD GFILKIKLGH    89
STAT 1         MSQWYELQQLDSKFLEQVHQ LYDDSFPM EIRQYLAQWLE KQDWEHAA---NDV--SFATI RFHDLSQLSQT DQYSRFSLE-- NNPELQHNIR    84
STAT 3         MAQWNQLQQLDTRYLEQLHQ LYSDS-FPM ELRQFLAPWIE SQDWAYAA---SKE--SHATL VPHNLGEID QQYSRFLQE- SNVLYQHNLR    84
STAT 2         MAQWEMLQNLDSPFQDQLHQ LYSHSLLPVDE FRQGHAALDE EALGLSDD--SKATM LFPHFLDQLN YECGRCSQDP ESILYQHNLR    88
STAT 4         MSQWNQVQQLEIKFLEQVDQ FYDDN-FPM EIRHLLAQWIE TQDWEVAS---NNE--THATI LQNLIQLD EQLGRVSKE-- KNLELIHNLK    84
Consensus      ...Q...QQL....L.Q..Q ...D..F.. .....R..... ....A...... --......AT. L...LE.... ....R...... ...HN..    90

IL-4 STAT (7/5)--HIST---- -------LES X----YQRDP LKLVAF---- FRQIL---QG EKK-AVMEQF RHLPMPFHWK QEELK----- ---FKTGLR-   135
STAT 5         YVHVSSRTRT TAAPWSWLRC XRHILYNEQR LVREATNGNS SAGILVDAMS QKHLQINQTF EELRLVTQDT ENELKKLQQT QEYFIIQYQE   179
STAT 1         KSKRNLQDNF QEDPIQMSMI LYSCLKEERK ILENAD---- -RFNQ--AQS GNIQSTVMLD KQKELDSKVR NVKDK-VMCI EHEIKSLEDL   166
STAT 3         RIKQFLQSRY LEKPMEIARI VARCLMEESR LLQTAA---- -TAAQQGGQA NHPTAAVVTE KQQMLEQHLQ DVRKR-VQDL EQKMKVVENL   169
STAT 2         KFCRDIQ-PF SQDPTQLAEM XFNLLLEEKR ILIQAQ---- -RAQL--EQG EPVLETPVES QQHEIESRIL DLRAM-MEKL VKSISQLKDQ   169
STAT 4         RIRKVLQGKF HGNPMHVAVV ESNCLRERR ILAMAN---- -MPIQ-GPLE KSLQSSSVSE RQRNVEHKVS AIKNS-VQMT EQDTKYLEDL   167
Consensus      ......Q... ...P...... X..L.HE.R .L..A.---- ....-....Q. ......-.... .........  ........K..     180

IL-4 STAT (7/5)--RLQHRVGE IHLL--REAL QKGA--EAGQ VSLHSLIETP ANGTGP-SEA LAHLLQETTG ELEAAKALVL KRIQI-WRRQ QQLAGNGXF   217
STAT 5         SLRIQAQFAQ LAQLNPQERL SRETALQQKQ VSLEAMLQRE AQTLQYYVE LAEKHQKTLQ LLRKQQTIIL DDELIQRR NIWRGMENM   268
STAT 1         QDEYDFKCKT LQNRE--HET NGVA--KSDQ KQEQLLLKKM YLMLDNKRKE VVHKIIELLN VTELTQNALI NDELVERR QQSACIGGF   252
STAT 3         QDDFDFNYKT LKSQGDMQDL NGNN--QSVT RQKMQQLEQM LTALDQMRRS IVSELAGLLS AMEYVQKTLT DEELADWKRR DQIACIGQP   256
STAT 2         QDVPCFRYK- IQAKG---KT PSLD--PHQT KEQK-ILQET LNELDKRKE VLDASKALG RLT-TLIELL VPKLEBME DQKACIRNE   251
STAT 4         QDEPDYRYKT IQTMD---QG DKNS--ILVN QEVLTLLQEM LNSLDFKRKE ALSKMTQIVN ETDLLMNSML LEELQDMR DQIACIGGL   252
Consensus      QD......K. .....-.... ......--... ......LD..R..........L. ......L .EL... RR QQ.ACIG.     270

IL-4 STAT (7/5)EESLAKEQER CESLVDIY-- ----SQLQQE VGAAG---GE L--------E AKTR--ASLT GRLDEVLRT VTSGE QXX PVLKTQ   286
STAT 5         PRSLDWLISW CEKLAEII-- ----WQNRQQ IRRAEHLCQQ LPIP-----G HVEEMLAEVN ATITDIISAL VTSAE DEE VLKTQ   345
STAT 1         NACIDQLQ-- ---------- ---------- VRQQLKKLEE LEQKYTYEHD PITKNKQVLW DRTFSLFQQL IQSNEV ENT HPQRP   321
STAT 3         NICQENN ITSLAESQLQ TRQQIKKLEE LHQKV----- ----SYKGD IVQHRPMLE ERIVELFRN MKSAEEL EVT MIPDRP   336
STAT 2         DHGLCHTW PTAGA----- ----KLLFH LRQLLKELKG LSCLVSYQD HLTKGVDLRN AQVTELLQRL HRAMH DPT HPRP   331
STAT 4         HNQLDQNC FTLLAESLPQ LRQQLEKLQE QSTKM----- ----TYEGD IPAQRAHLL ERATPLIYN FKNSFV DGT HPQRP   332
Consensus      ...ILQ... ...LA...-- -....,...... .............L....Y..D ......L. .R...L... ..S.VD.... ..P.RP    360

IL-4 STAT (7/5)TKFQAGVRFL LGLKFL-GAP AKPPLVRADM VTEKQARELS VPQGPGAGAE STGEEIIINNTV PLENSIPGNC CSALPKNLLL KKIKRCERKG   375
STAT 5         TKFAAVWRLL VGGKL--NVH MNPPQAKATI ISHQQAKSL- -LKNENTRNE CSGEILNNCC VMEYHQRTGT LSAHFRNMSL KRIKRADRRG   431
STAT 1         LVLKTGVQFT VKLRLLLVKLQ ELNYNIKKV LFKDUVERN TVKGFRKFNI LGTHTKVMNM EESTNGSLAA EPRHLQLKEQ K-NAGTRTN-   409
STAT 3         LVIKTGVQFT TKVRLLVRFP ELNYQLKIKV CIDKDSGDVA ALRGSRKFNI LGTNTKVMNM EESNNGSLSA EPRKHLTLREQ KCGNGGRANC   426
STAT 2         LILKTGSKFT VRTRLLVRLQ EGNESITVEV SIDRNPPQ-- -LQGFRKFNI LTSNQKTLTP EKGOSQGLIW DPFGYLTLVEQ RSGGSGKGSN   418
STAT 4         MVLKTIIQFT VKLNLLIKLP ELNYQVKVKA SIDRNVST-- -LSN--RRFVL CGTHVKAMSS EESSNGSLSV EPRHLQPKEM KCSTGSGKGN-   417
Consensus      ...KTGV.PT V..RLL.... E.N..K... .DK...... .L.G.R.FN. ....K..... E..S..L... .P.HL...E. K.........    450

IL-4 STAT (7/5)TESVTEEKCA VLFSASFTLG PGMKPIDLQA LEFFV GADNNNAW FILWAF-SE MDRVP-HVVA ERVPWEKMCE TLNLKFMAEV   463
STAT 5         AESVTEEKFT VLPESQFSVG SNMLPFVKT ISLVHKT GSDHNATV VLWAP-AE PGRVP-EAVP DKVLWPQLCE AIANKPKAEV   519
STAT 1         EGPLIVTEEL HSLSFFETQLC QPGLIDEFT VSLVHKT IPNAWAI LAINLTN PRNLSFFLTP PCARWAQLSE VLSWQFSSVT   499
STAT 3         DASLIVTEEL HLITFFETEVY HQGEKIDEFT ISMVHKT ICGMPNAI LAINLTN PKNVNEFKP PIGTWDQVAE VLSWQFSSTT   516
STAT 2         KGPLGVTEEL HIISFPTVKYT YQCKQLHKT ISHVMLSN VDPRLLSPN KPKAPSIAAP PKAPWSLGP ALSWQFSYV   508
STAT 4         EGCHMVTEEL HSITFETQIC LYGEDIMLEF ISLQMVQSLL PNAWAI LAISTND SQNVRFNFNP PSVTLGQELE VMSWQFSSYV   507
Consensus      .....VTEEL H....F.... ....G.ILL.T ........... ..NAWAS .ILN.... ....N..F.. .P...W.QL.E .LSWQFS.V   540

IL-4 STAT (7/5)GTNRGILPEH FLFLTACEEN DNSLSMEAFQ HRSVSQGEN KEILLGRGFT FWRDCVLD LTKRCLRSVW SDRIRYEKS KQYVTSHLN   553
STAT 5         QSNPGLTKEN LLFLTACEPN NSSSHLEDYN GHVSQGEN KENLPGNYT HIFGVME VLKKHHKPH NDGHLIEFIS KQQAHDILIN   609
STAT 1         --MRGLVPDQ LAMRALEELG PNA----SPD G-LIFEFT KENINDKNFP HMLELILE LIKKHLLPIW NIGQIREPIS KERERAKLKD   582
STAT 3         --MRGLSIEQ LNMLGELLG PGV---NYS GCQITMNAVL KENMAGKGPS MAILDKILE LVKKYILAIN NEGYNINMEFIS KEREKARNHI   600
STAT 2         --QRGINSDQ LSMRNLFLG QNC----RTE DPLLSNADET KRESPPGKLP MDLKILE LVHDHLKDLM VDGINRFEFS RSQERRLLKD   592
STAT 4         --QRGINSBD LNMLAFKLV QS----NYM DGHLPERFT KEHLPGKTFT MLEATILD LIKKHILPLM LDGYMGRAFS KEKERLLKD   590
Consensus      --.RGI..EQ L..L..A... ......... ..........  KE...G..F. H..D..VLD .L..KHH... L..G..IPFIS .K...ER.I.I   630

IL-4 STAT (7/5)EPIGTFLLRF SESICKG-XT AHVIR-GQD GSPQIPEHNICP FSAKDLSIRS LGDRIRDLAQ LK-NLYPKKP KDEAPRSHYK PEQMGKDCRG   640
STAT 5         KPIGTFLLRF SESICGG-XT ANKPD-SPD --RNLMELVR MTKKELSAVT FPDIIRNYKV NAAENIPEN KKYLYPNIDK DHAFGKYY--   670
STAT 1         QQFGTFLLRF SESKKEGT FTWVERSQNG GEPDFHAVER MTKKELSAVT FPDIIRNYKV NAAENIPENP KKYLYPNIDK DHAFGKYY--   678
STAT 3         KPFGTFLLRF SESKREGA FTWVEK-DIS GKTQIQSVEP LTKQQLNNHS FAEIIMGYKI MDATNILLSF PVYLYPIDIPK EEAFGKY---   686
STAT 2         TMSGTFLLRF SESIGG-XT SWVEH-QDD DKVLIYSVEP LTKEVLQSLP LTEITHRVQL LMAINIPENP KKYLYPRIPR DEAFGCYYQE   680
STAT 4         KMEGTFLLRF SESHLGG-XT TWVDQSENG S-VRFHSVEP TNKGRISALA FADILRDYKV IMAENIPENP KKYLYPDIPK DKAFGKYY--   676
Consensus      ...GTFLLRF SESI.GG-XT .WV..-.... ..........P .TK..LS... .DIIR.Y.. ....NIP..P ..LYP.I.K ..AFGK....   720

IL-4 STAT (7/5)YVPATIKMTV ERDQPLPTPE LQMPTMVPSY DLGMAPDSSH SMQLGPDMVP QVYPPHSHSI PPYQGLSPEE SVNVLSAFQE PHLQMPPSLG   730
STAT 5         YVKPQIK--- ---------- ----QVVPEF -VSASADSA- ----GS---- ---------- ---------- ---------- RHLH------   720
STAT 1         -----SRPK- ---------- ----EAPEP- -MELDGPKG- ---------- ---------- ---------- ---------- -T GYIKTEL---   695
STAT 3         -----CRP-- ---------- ----ESQEH- -PEADPGSA- ---------- ---------- ---------- ---------- -A PYLKTKF---   710
STAT 2         KVNLQERRKY LKIHRLIVVSN RQVDELQQP- -LELKPEPE- ---------- ---------L ESLELELGLV PEPELSDLE PLLKAGLDLG   748
STAT 4         ----SSQPC- ---------- ----EVSRP- -TE-RGDKG- ---------- ---------- ---------- ---------- -YVPSVF---   699
Consensus      ----.....- ---------- ----E....- -.E...- ---------- ---------- ---------- ---------- ..L.......   810

IL-4 STAT (7/5)QMSLPFDQPH PQGLLPCQPQ EHAVSSPDPL LCSDVTMVED SCLSQPVTAF PQGTWIGEDI FPPLLPPTEQ DLTKLLLEGQ GESGGGSLGA   820
STAT 5         ---------- ---------- -------- ---------- ---------- ---------- ---------- ---------- -PSRVPP-- ---- ---- ASL--   734
STAT 1         ---------- ---------- --------IS -VSEVHPSRL Q------TTD NLLP-----M SPEEFD---- -EVSRIVGS VE-------- ----FDSM--   735
STAT 3         ---------- ---------- --------IC -VTPTTCS-- N-------TID --LP-----M SPRALD---- -SLMQFGNN GE---GAEPS AGGQFESLTF   757
STAT 2         PELESVLEST LEPVIEPTLC MVSQTVPEPD QGPVSQPVPE PDLPCDLRHL NTEPMEIFRN CVKIEEIMPN GDPLLAGQNT VDEVYVSRPS   838
STAT 4         ---------- ---------- --------IP -ISTIRSDST E------PQSPS DLLP-----M SPSAYA---- --VLRENLSP TT-------- ----IETA--   741
Consensus      ---------- ---------- ...-...... P... .----..... ..LP----- ---------- ---------- ---------- ......S...   900

IL-4 STAT (7/5)QPLLQPSHYG QSGISMSHMD LRANPSWX                                                                    848
STAT 5         ---------- -------- -.                                                                              734
STAT 1         --M------- -NTVX---- --------                                                                       740
STAT 3         D-MELTSPCA TSPMX----- --------                                                                      771
STAT 2         H-FYTDGPLM PSDFX----- --------                                                                      852
STAT 4         --MN-----S PYSAE----- --------                                                                      749
Consensus      .-........ ....,----- --------                                                                      928
```

In all cases, the most significant segments of sequence similarity corresponded to three regions, one consisting of roughly 50 amino acids located at the amino termini of all six proteins and two more centrally located regions that have been predicted to specify SH2 and SH3 domains. Given the high degree of relatedness of the IL-4 induced protein to Stat proteins, coupled with its rapid, phosphotyrosine associated conversion from latent to active state, we have designated this protein IL-4 Stat.

Northern blotting assays confirmed the presence of an IL-4 Stat mRNA approximately 4 kilobases in length. This mRNA species was observed in a wide variety of human tissues, with highest levels occurring in placenta, lung, liver, kidney, thymus, prostate, ovary and peripheral blood lymphocytes. Northern blotting also revealed a slightly smaller mRNA that was observed most abundantly in kidney. Three larger mRNA species roughly 4.8, 5.5 and 6 kilobases in length were also observed. The 4.8 and 6 kilobase species were observed most abundantly in spleen and thymus, whereas the 5.5 kilobase species was only observed in peripheral blood lymphocytes.

Inhibition of IL-4 Stat DNA Binding Activity by Receptor Peptides

The IL-4 receptor complex is composed of two distinct polypeptides, a 139 Kd ligand binding subunit (IL-4R) and a smaller polypeptide (IL-2Rg) also utilized for IL-2 and IL-13 signaling (Ohara and Paul, 1987; Mosley et al., 1989; Noguchi et al., 1993; Russell et at., 1993). Inspection of the primary amino acid sequences of the intracellular domains of the two receptor subunits has not revealed obvious motifs capable of mediating signal transduction. IL-4 treatment of cultured cells does, however, bring about rapid tyrosine phosphorylation of the intracellular domain of the IL-4R subunit (Wang et at., 1992; Izuhara and Harada, 1993). Indeed, phosphorylation of tyrosine residue 472 (Y472) of the IL-4R has recently been implicated in signaling through a large cytoplasmic protein variously termed insulin receptor substrate-1 (IRS-1) or 4PS (Keegan et at., 1994). Having noted that the primary amino acid sequence of IL-4 Stat may specify an SH2 domain, we considered whether this domain might facilitate direct interaction with the intracellular domain of the IL-4 receptor at some point in the IL-4 Stat activation cycle.

In order to investigate possible coupling between the IL-4 receptor and the transcription factor it appears to activate, we examined the inhibitory effects of five phosphotyrosine peptides derived from the intracellular domain of the human IL-4R receptor on DNA binding by activated IL-4 Stat. As a control we also tested the inhibitory activity of the phosphotyrosine peptide of the IFN-g receptor that had previously been shown to potently block p91 activation (Greenlund et al., 1994). Each peptide contained a centrally located phosphotyrosine flanked on NH2 and COOH sides by seven amino acids specified by the native sequence of the human IL-4R subunit (Mosley et al., 1989; Takeshita et al., 1992). Samples of nuclear extract prepared from IL-4 induced Thp-1 cells were incubated with individual phosphopeptides then tested by the gel mobility shift assay for the retention of active IL-4 Stat. Two of the five phosphopeptides derived from the intracellular domain of the IL-4R subunit inhibited the DNA binding activity of IL-4 Stat at concentrations ranging from 100 to 300 uM. The IFN-g derived phosphopeptide did not affect DNA binding activity. Moreover, the activities of both of the inhibitory, IL-4R derived peptides were critically dependent upon tyrosine phosphorylation. Non-phosphorylated peptides showed no inhibitory activity.

Surprisingly, the two inhibitory peptides derived from the IL-4R are related in primary amino acid sequence, (NH2-GPPGEAGYKAFSSLL(SEQ ID NO:10)-COOH and NH2-ASSGEEGYKPFQDLI(SEQ ID NO:11)-COOH). It is notable that, relative to the centrally located phosphotyrosine, the two peptides are identical at the +1 and +3 positions. Detailed studies of SH2:phosphytyrosine peptide interaction have suggested that the +1 and +3 positions may be important for specifying selectivity of phosphotyrosine peptide:SH2 interaction (Songyang et al., 1993; Marengere et al., 1994).

To test whether the IL-4 receptor derived phosphopeptides might interact directly with IL-4 Stat, we examined the effects of five synthetic peptides on the DNA binding activity of the purified transcription factor. IL-4 Stat purified from IL-4 induced Thp-1 cells was incubated with the two IL-4 receptor-derived phosphopeptides that had shown inhibitory activity when tested in crude nuclear extracts. Corresponding non-phosphorylated versions of each peptide were also assayed, as was the tyrosine phosphorylated peptide derived from the IFN-g receptor that had been shown to inhibit activation of p91 in previous studies (Greenlund et al., 1994). We again observed phosphotyrosine dependent inhibition by the two IL-4R derived peptides and no discernible inhibitory effect by the IFN-g phosphopeptide.

As judged by Coomassie staining, the IL-4 Stat used in the present study was pure. Given that the two receptor-derived, inhibitory peptides were capable of complete elimination of IL-4 Stat DNA binding activity, any indirect mode of inhibition must invoke a catalytic mechanism. One such mechanism might entail dephosphorylation of IL-4 Stat, a possibility eliminated by immunoblot assays using antibodies specific to phosphotyrosine. Following complete inhibition of IL-4 Stat DNA binding activity by incubation with 300uM of the inhibitory phosphopeptides, protein was analyzed by Western blotting using anti-phosphotyrosine antibodies. As judged by this assay, IL-4 Stat does not lose phosphotyrosine as a result of exposure to the receptor-derived, inhibitory peptides.

Receptor-derived phosphotyrosine peptides inhibit IL-4 Stat dimerization

How might the inhibitory peptides derived from the IL-4 receptor block the DNA binding activity of purified IL-4 Stat? The inhibitory activity of both receptor-derived peptides required phosphorylation on tyrosine. Moreover, the inhibitory peptides were related in primary amino acid sequence on the immediate carboxyl terminal side of the phosphorylated tyrosine, a region which may play a role in specifying interaction between phosphotyrosine peptides and SH2 domains (Songyang et al., 1993). We imagined that these inhibitory peptides might bind to the SH2 domain of IL-4 Stat, thereby disrupting the reciprocal SH2:phosphotyrosine interactions that otherwise facilitate dimer adherence.

In order to test whether IL-4 Stat indeed exists in a dimeric state, purified protein was exposed independently to two chemical crosslinkers, glutaraldehyde and DSG. Both reagents caused time dependent crosslinking of IL-4 Stat to covalently linked dimers. Even when exposed for a length of time sufficient to quantitatively crosslink all IL-4 Stat to eovalently linked dimers, no evidence of higher order (trimeric or tetrameric) oligomerization was observed. The limit nature of this cross linking, coupled with the fact that it was observed at a very low protein concentration, provides firm evidence that functional IL-4 Stat exists in a dimeric state. This interpretation is consistent with studies of other Stat proteins (Shuai et at., 1994). It likewise fits with the dyad symmetric nature of the seven IL-4 Stat binding sites identified thus far (Koranides and Reich, 1993).

Chemical crosslinking provided a means of testing whether the monomer:dimer equilibrium of IL-4 Stat might be influenced by the IL-4 receptor-derived peptides that were observed to inhibit DNA binding. Purified IL-4 Stat was exposed to the same five peptides that were tested in the DNA binding inhibition assay. Following a brief incubation interval the samples were exposed to DSG under conditions sufficient to quantitatively crosslink IL-4 Stat. The two IL-4 receptor derived peptides, if phosphorylated on tyrosine, impeded formation of covalently linked IL-4 Stat in a concentration dependent manner. No effect was observed when non-phosphorylated variants of the same two peptides were tested. Likewise, the phosphopeptide derived from the IFN-g receptor did not impede DSG-mediated cross linking. The concentration at which receptor-derived phosphopeptides inhibit DNA binding corresponds closely with that required to impede crosslinking of IL-4 Stat dimers. We therefore conclude that incubation of IL-4 Stat with tyrosine phosphorylated peptides derived from the intracellular domain if its cognate receptor influences monomer:dimer equilibrium, and that the disassociation of IL-4 Stat dimers represents the mechanism by which receptor-derived phosphopeptides inhibit DNA binding.

From the foregoing observations, we conclude that IL-4 Stat activation entails transient coupling with either or both of two specific tyrosine residues, Y578 and Y606, located in the intracellular domain of the IL-4 receptor. Given that the inhibitory activities of synthetic peptides corresponding to these regions of the IL-4 receptor require tyrosine phosphorylation, transient receptor coupling of IL-4 Stat is likewise be dependent upon tyrosine phosphorylation. These findings are at odds with functional studies of the IL-4R subunit which have shown that mutated variants of the receptor lacking all tyrosines native to the intracellular domain can mediate the growth stimulatory effects of IL-4 as tested in the murine pro-B cell line, Ba/F3 (Seldin and Leder, 1994). Surprisingly, the readout of the Ba/F3 assay, mitotic proliferation, must also be independent of IL-4 mediated activation of IRS-1. Tyrosine 472 of the IL-4R subunit has been firmly implicated in the IL-4 induced phosphorylation of IRS-1 and proliferative response of human macrophage 32D cells (Keegan et al., 1994).

A second conclusion from the studies reported herein derives from the ability of IL-4 receptor-derived phosphopeptides to selectively inhibited DSG-mediated crosslinking of IL-4 Stat. Such inhibition was observed at concentrations similar to those required to inhibit DNA binding activity. These results indicate that the inhibitory peptides dissociate IL-4 Stat dimers, thereby causing an inhibition of DNA binding activity. We further conclude that IL-4 Stat utilizes the same polypeptide domain to mediate transient receptor interaction and dimerization.

The following examples are offered by way of illustration and not by way of limitation.

EXAMPLES

1. Protocol for IL-4 Stat—IL-4 Stat dependent transcription factor binding assay.
A. Reagents:
  IL-4 Stat: 20 µg/ml activated, truncated (SH2 domain) IL-4 Stat in PBS.
  Blocking buffer: 5% BSA, 0.5% Tween 20 in PBS; 1 hr, RT.
  Assay Buffer: 100 mM KCl, 20 mM HEPES pH 7.6, 0.25 mM EDTA, 1% glycerol, 0.5 % NP-40, 50 mM BME, 1 mg/ml BSA, cocktail of protease inhibitors.
  $^{33}$P IL-4 Stat 10x stock: $10^{-8}$–$10^{-6}$M "cold" IL-4 Stat homolog supplemented with 200,000–250,000 cpm of labeled IL-4 Stat homolog (Beckman counter). Place in the 4° C. microfridge during screening.
  Protease inhibitor cocktail (1000X): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2mM NaVo$_3$ (Sigma #S-6508) in 10 ml of PBS.
B. Preparation of assay plates:
  Coat with 120 µl of stock IL-4 Stat per well overnight at 4° C.
  Wash 2X with 200 µl PBS.
  Block with 150 µl of blocking buffer.
  Wash 2X with 200 µl PBS.
C. Assay:
  Add 80 µl assay buffer/well.
  Add 10 µl compound or extract.
  Add 10 µl $^{33}$P-IL-4 Stat (20,000–25,000 cpm/0.3 pmoles/well=3×$10^{-9}$M final concentration).
  Shake at 25C. for 15 min.
  Incubate additional 45 min. at 25C.
  Stop the reaction by washing 4X with 200 µl PBS.
  Add 150 µl scintillation cocktail.
  Count in Topcount.
D. Controls for all assays (located on each plate):
  a. Non-specific binding (no IL-4 Stat added)
  b. cold IL-4 Stat at 80% inhibition.

2. Protocol for IL-4 Stat—IL-4 Receptor-peptide binding assay.
A. Reagents:
  Neutralite Avidin: 20 µg/ml in PBS.
  Blocking buffer: 5% BSA, 0.5% Tween 20 in PBS; 1 hr, RT.
  Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
  $^{33}$P IL-4 Stat 10x stock: $10^{-8}$–$10^{-6}$M "cold" inactive (not tyr-phosporylated) and truncated (SH2 domain) IL-4 Stat supplemented with 200,000–250,000 cpm of labeled, inactive and truncated IL-4 Stat (Beckman counter). Place in the 4° C. microfridge during screening.
  Protease inhibitor cocktail (1000X): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.
  IL-4-receptor-peptides: $10^{-8}$–$10^{-5}$M of each IL-4 receptor biotinylated peptides: NH$_2$-GPPGEAGYKAFSS-LL(SEQ ID NO:10)-COOH AND NH$_2$-ASSGEEGYK-PFQDLI(SEQ ID NO: 11)-COOH in PBS.
B. Preparation of assay plates:
  Coat with 120 µl of stock N-Avidin per well overnight at 4° C.
  Wash 2X with 200 µl PBS.
  Block with 150 µl of blocking buffer.
  Wash 2X with 200 µl PBS.
C. Assay:
  Add 40 µl assay buffer/well.
  Add 10 µl compound or extract.
  Add 10 µl $^{33}$P-IL-4 Stat (20,000–25,000 cpm/0.1–10 pmoles/well=$10^{-9}$–$10^{-7}$M final concentration).
  Shake at 25C. for 15 min.
  Incubate additional 45 min. at 25C.
  Add 40 µl IL-4 Stat receptor peptide mixture (0.1–10 pmoles/40 ul in assay buffer)

Incubate 1 hr at RT.
Stop the reaction by washing 4X with 200 µl PBS.
Add 150 µl scintillation cocktail.
Count in Topcount.

D. Controls for all assays (located on each plate):
 a. Non-specific binding (no receptor peptide added)
 b. Soluble (non-biotinylated receptor peptide) at 80% inhibition.

3. Protocol for IL-4 Stat dependent transcription factor—DNA binding assay.

A. Reagents:
Neutralite Avidin: 20 µg/ml in PBS.
Blocking buffer: 5% BSA, 0.5% Tween 20 in PBS; 1 hr, RT.
Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
$^{33}$P IL-4 Stat 10x stock: $10^{-6}$–$10^{-8}$M "cold" IL-4 Stat (see above) supplemented with 200,000–250,000 cpm of labeled IL-4 Stat (Beckman counter). Place in the 4° C. microfridge during screening.
Protease inhibitor cocktail (1000X): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.
Oligonucleotide stock; (specific biotinylated). Biotinylated oligo at 17 pmole/µl, IL-4 Stat binding site: (BIOTIN)-GTATTTCCCAGAAAAGGAAC(SEQ ID NO:03)

B. Preparation of assay plates:
Coat with 120 µl of stock N-Avidin per well overnight at 4° C.
Wash 2X with 200 µl PBS.
Block with 150 µl of blocking buffer.
Wash 2X with 200 µl PBS.

C. Assay:
Add 40 µl assay buffer/well.
Add 10 µl compound or extract.
Add 10 µl $^{33}$P-IL-4 Stat (20,000–25,000 cpm/0.1–10 pmoles/well=$10^{-9}$–$10^{-7}$M final concentration).
Shake at 25C. for 15 min.
Incubate additional 45 min. at 25C.
Add 40 µl oligo mixture (1.0 pmoles/40 ul in assay buffer with 1 ng of ss-DNA)
Incubate 1 hr at RT.
Stop the reaction by washing 4X with 200 µl PBS.
Add 150 µl scintillation cocktail.
Count in Topcount.

D. Controls for all assays (located on each plate):
 a. Non-specific binding (no oligo added)
 b. Specific soluble oligo at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

| IL-4 Stat cDNA (SEQUENCE ID NOS: 01 and 02) | | | | | |
|---|---|---|---|---|---|
| 10<br>1234567890 | 20<br>1234567890 | 30<br>1234567890 | 40<br>1234567890 | 50<br>1234567890 | 60<br>1234567890 |
| ATCTTATTTT | TCTTTTTGGT | GGTGGTGGTG | GAAGGGGGGA | GGTGCTAGCA | GGGCCAGCCT |
| AGTGCCCGCT | GAGAAAGGGA | GAAGACAGCA | GAGGGGTTGC | CGAGGCAACC | TCCAAGTCCC |
| AGAAAAAGTG<br>E K V | CAGCGGCTCT<br>Q R L Y | ATGTCGACTT<br>V D F | TCCCCAACAC<br>P Q H | CTGCGGCATC<br>L R H L | TTCTGGGTGA<br>L G D |
| GACGCCTTCT<br>D A F C | GCTGCAACTT<br>C N L | GGCTAGTGCC<br>A S A | CTACTTTCAG<br>L L S D | ACACTGTCCA<br>T V Q | GCACCTTCAG<br>H L Q |
| AACACATCAG<br>H I S | CACCCTTGAG<br>T L E | AGCATATATC<br>S I Y Q | AGAGGGACCC<br>R D P | CCTGAAGCTG<br>L K L | GTGGCCATCTT<br>V A T F |
| ACAGTTCCGC<br>Q F R | CACTTGCCAA<br>H L P M | TGCCTTTCCA<br>P F H | CTGGAAGCAG<br>W K Q | GAAGAACTCA<br>E E L K | AGTTTAAGAC<br>F K T |
| CTTCTCCGAG<br>L L R E | AAGCCCTGCA<br>A L Q | GAAGGGGCT<br>K G A | GAGGCTGCC<br>E A G Q | AAGTGTCTCT<br>V S L | GCACAGCTTG<br>H S L |
| TGGCCATGCT<br>A M L | ACTGCAGGAG<br>L Q E | ACCACTGGAG<br>T T G E | AGCTAGAGGC<br>L E A | AGCCAAAGCC<br>A K A | CTAGTGCTGA<br>L V L K |
| GAATGGCGCA<br>N G A | CCGTTTGAGG<br>P F E E | AGAGCCTGGC<br>S L A | CCCACTCCAG<br>P L Q | GAGAGGTGTG<br>E R C E | AAAGCCTGGT<br>S L V |
| GGTGGGGAGC<br>G G E L | TTGAGCCCAA<br>E P K | GACCCGGGCA<br>T R A | TCGCTGACTG<br>S L T G | GCCGGCTGGA<br>R L D | TGAAGTCCTG<br>E V L |
| CCCCCCAGGT<br>P Q V | ACTGAAGACT<br>L K T | CAGACCAAGT<br>Q T K F | TCCAGGCTGG<br>Q A G | AGTTCGATTC<br>V R F | CTGTTGGGCT<br>L L G L |
| GGCCGACATG | GTGACAGAGA | AGCAGGCGCG | GGAGCTGAGT | GTGCCTCAGG | GTCCTGGGGC |

| IL-4 Stat cDNA (SEQUENCE ID NOS: 01 and 02) | | | | | |
|---|---|---|---|---|---|
| A D M | V T E K | Q A R | E L S | V P Q G | P G A |
| CCCTTGGAGA | ACAGCATTCC | TGGGAACTGC | TGCTCTGCCC | TGTTCAAGAA | CCTGCTTCTC |
| P L E N | S I P | G N C | C S A L | F K N | L L L |
| TCACAGAGGA | GAAGTGCGTCT | GTGCTCTTCT | CTGCCAGCTT | CACACTTGGC | CCCGGCAAAC |
| T E E | K C A | V L F S | A S F | T L G | P G K L |
| CATCGTCCAT | GGCAACCAAG | ACAACAATGC | CAAAGCCACT | ATCCTGTGGG | ACAATGCCTT |
| I V H | G N Q D | N N A | K A T | I L W D | N A F |
| GTGCCCTGGG | AGAAGATGTG | TGAAACTCTG | AACCTGAAGT | TCATGGCTGA | GGTGGGGACC |
| V P W E | K M C | E T L | N L K F | M A E | V G T |
| AGAAGATCTT | CAATGACAAC | AGCCTCAGTA | TGGAGGCCTT | CCAGCACCGT | TCTGTGTCCT |
| K I F | N D N | S L S M | E A F | Q H R | S V S W |
| CACCTTTTGG | CAGTGGTTTG | ATGGTGTCCT | GGACCTCACC | AAACGCTGTC | TCCGGAGCTA |
| T F W | Q W F D | G V L | D L T | K R C L | R S Y |
| TACGTTACTA | GCCTTCTTCT | CAATGAGCCC | GACGGAACCT | TTCTCCTCCG | CTTCAGCGAC |
| Y V T S | L L L | N E P | D G T F | L L R | F S D |
| GCCAGGATGG | CTCTCCACAG | ATAGAGAACA | TCCAGCCATT | CTCTGCCAAA | GACCTGTCCA |
| Q D G | S P Q | I E N I | Q P F | S A K | D L S I |
| CAAAAATCTC | TATCCCAAGA | AGCCCAAGGA | TGAGGCTTTC | CGGAGCCACT | ACAAGCCTGA |
| K N L | Y P K K | P K D | E A F | R S H Y | K P E |
| ATCAAGATGA | CCGTGGAAAG | GGACCAACCA | CTTCCTACCC | CAGAGCTCCA | GATGCCTACC |
| I K M T | V E R | D Q P | L P T P | E L Q | M P T |
| CCATGAGCAT | GCAGCTTGGC | CCAGATATGG | TGCCCCAGGT | GTACCCACCA | CACTCTCACT |
| M S M | Q L G | P D M V | P Q V | Y P P | H S H S |
| CAACGTGTTG | TCAGCCTTCC | AGGAGCCTCA | CCTGCAGATG | CCCCCCAGCC | TGGGCCAGAT |
| N V L | S A F Q | E P H | L Q M | P P S L | G Q M |
| CCGTGCCAGC | CTCAGGAGCA | TGCTGTGTCC | AGCCCTGACC | CCCTGCTCTG | CTCAGATGTG |
| P C Q P | Q E H | A V S | S P D P | L L C | S D V |
| CGTTTCCTCA | GGGCACTTGG | ATTGGTGAAG | ACATATTCCC | TCCTCTGCTG | CCTCCCACTG |
| F P Q | G T W | I G E D | I F P | P L L | P P T E |
| GTCGGGGGGA | GGGTCCTTGG | GGGCACAGCC | CCTCCTGCAG | CCCTCCCACT | ATGGGCAATC |
| S G G | G S L G | A Q P | L L Q | P S H Y | G Q S |
| AGTTGGTGAT | CCCAGCTGGA | GGGAGAACCC | AAAGAGACAG | CTCTTCTACT | ACCCCCACAG |
| ATGGGGAGGG | TGCCCTCCTA | TCCCCACCTA | CTCCTGGGTC | AGGAGGAAAA | GACTAACAGG |
| TATCATTCCC | CTGCCCACCT | CCTTCCAGCA | CTGACTGGAA | GGGAAGTTCA | GGCTCTGAGA |
| GCACACACAC | ATACAGAGCT | CTCTGAGGGT | GATGGGGCTG | AGCAGG | |

| | 70<br>1234567890 | 80<br>1234567890 | 90<br>1234567890 | 100<br>1234567890 | |
|---|---|---|---|---|---|
| | TGAACTCGCT | GGACAGAGCT | ACAGACCTAT | GGGGCCTGGA | 100 |
| | AGATCATGTC<br>M S | TCTGTGGGGT<br>L W G | CTGGTCTCCA<br>L V S K | AGATGCCCCC<br>M P P | 200 |
| | CTGGCTGGAG<br>W L E | AGCCAGCCCT<br>S Q P W | GGGAGTTCCT<br>E F L | GGTCGGCTCC<br>V G S | 300 |
| | GCCTCGGTGG<br>A S V G | GAGAGCAGGG<br>E Q G | GGAGGGGAGC<br>E G S | ACCATCTTGC<br>T I L Q | 400 |
| | TCAGACAAAT<br>R Q I | ACTTCAAGGA<br>L Q G | GAGAAAAAAG<br>E K K A | CTGTTATGGA<br>V M E | 500 |
| | AGGCTTGCGG<br>G L R | AGGCTGCAGC<br>R L Q H | ACCGAGTAGG<br>R V G | GGAGATCCAC<br>E I H | 600 |
| | ATAGAAACTC<br>I E T P | CTGCTAATGG<br>A N G | GACTGGGCCA<br>T G P | AGTGAGGCCC<br>S E A L | 700 |
| | AGAGGATCCA<br>R I Q | GATTTGGAAA<br>I W K | CGGCAGCAGC<br>R Q Q | AGCTGGCAGG<br>L A G | 800 |

| IL-4 Stat cDNA (SEQUENCE ID NOS: 01 and 02) | | | | |
|---|---|---|---|---|
| GGACATTTAT<br>D  I  Y | TCCCAGCTAC<br>S  Q  L  Q | AGCAGGAGGT<br>Q  E  V | AGGGGCGGCT<br>G  A  A | 900 |
| AGAACCCTCG<br>R  T  L  V | TCACCAGTTG<br>T  S  C | CTTCCTGGTG<br>F  L  V | GAGAAGCAGC<br>E  K  Q  P | 1000 |
| TGAGGTTCCT<br>R  F  L | GGGGGCCCCA<br>G  A  P | GCCAAGCCTC<br>A  K  P  P | CGCTGGTCAG<br>L  V  R | 1100 |
| TGGAGCAGAA<br>G  A  E | AGCACTGGAG<br>S  T  G  E | AAATCATCAA<br>I  I  N | CAACACTGTG<br>N  T  V | 1200 |
| AAGAAGATCA<br>K  K  I  K | AGCGGTGTGA<br>R  C  E | GCGGAAGGGC<br>R  K  G | ACTGAGTCTG<br>T  E  S  V | 1300 |
| TCCCCATCCA<br>P  I  Q | GCTCCAGGCC<br>L  Q  A | CTGTCTCTGC<br>L  S  L  P | CCCTGGTGGT<br>L  V  V | 1400 |
| CTCTGAGATG<br>S  E  M | GACCGCGTGC<br>D  R  V  P | CCTTTGTGGT<br>F  V  V | GGCTGAGCGG<br>A  E  R | 1500 |
| AACCGGGGGC<br>N  R  G  L | TGCTCCCAGA<br>L  P  E | GCACTTCCTC<br>H  F  L | TTCCTGGCCC<br>F  L  A  Q | 1600 |
| GGTCGCAGTT<br>S  Q  F | CAACAAGGAG<br>N  K  E | ATCCTGCTGG<br>I  L  L  G | GCCGTGGCTT<br>R  G  F | 1700 |
| CTGGTCTGAC<br>W  S  D | CGGCTGATCA<br>R  L  I  I | TTGGCTTCAT<br>G  F  I | CAGCAAACAG<br>S  K  Q | 1800 |
| TCAGAGATTG<br>S  E  I  G | GGGGCATCAC<br>G  I  T | CATTGCCCAT<br>I  A  H | GTCATCCGGG<br>V  I  R  G | 1900 |
| TTCGCTCACT<br>R  S  L | GGGGGACCGA<br>G  D  R | ATCCGGGATC<br>I  R  D  L | TTGCTCAGCT<br>A  Q  L | 2000 |
| ACAGATGGGT<br>Q  M  G | AAGGATGGCA<br>K  D  G  R | GGGGTTATGT<br>G  Y  V | CCCAGCTACC<br>P  A  T | 2100 |
| ATGGTGCCTT<br>M  V  P  S | CTTATGACCT<br>Y  D  L | TGGAATGGCC<br>G  M  A | CCTGATTCCT<br>P  D  S  S | 2200 |
| CCATCCCCCC<br>I  P  P | GTATCAAGGC<br>Y  Q  G | CTCTCCCCAG<br>L  S  P  E | AAGAATCAGT<br>E  S  V | 2300 |
| GAGCCTGCCC<br>S  L  P | TTTGACCAGC<br>F  D  Q  P | CTCACCCCCA<br>H  P  Q | GGGCCTGCTG<br>G  L  L | 2400 |
| ACCATGGTGG<br>T  M  V  E | AAGACAGCTG<br>D  S  C | CCTGAGCCAG<br>L  S  Q | CCAGTGACAG<br>P  V  T  A | 2500 |
| AACAGGACCT<br>Q  D  L | CACTAAGCTT<br>T  K  L | CTCCTGGAGG<br>L  L  E  G | GGCAAGGGGA<br>Q  G  E | 2600 |
| TGGGATCTCA<br>G  I  S | ATGTCCACA<br>M  S  H  M | TGGACCTAAG<br>D  L  R | GGCCAACCCC<br>A  N  P | 2700 |
| ACCTGCTCTG<br>AGAATGCACA<br>CACGCCCCAA | GACACTTGCT<br>GTGGGTGGAG<br>CATGCCTGCA | CATGCCCTGC<br>CCAATCCACT<br>CCTGCAGCGC | CAAGCAGCAG<br>CCTTCCTTTC<br>GCACACGCAC | 2800<br>2900<br>3000<br>3046 |

| IL-4 Stat protein (SEQUENCE ID NO: 2) | | | | | |
|---|---|---|---|---|---|
| 10<br>1234567890 | 20<br>1234567890 | 30<br>1234567890 | 40<br>1234567890 | 50<br>1234567890 | |
| MSLWGLVSKM | PPEKVQRLYV | DFPQHLRHLL | GDWLESQPWE | FLVGSDAFCC | 50 |
| NLASALLSDT | VQHLQASVGE | QGEGSTILQH | ISTLESIYQR | DPLKLVATFR | 100 |
| QILQGEKKAV | MEQFRHLPMP | FHWKQEELKF | KTGLRRLQHR | VGETHLLREA | 150 |
| LQKGAEAGQV | SLHSLIETPA | NGTGPSEALA | MLLQETTGEL | EAAKALVLKR | 200 |
| IQIWKRQQQL | AGNGAPFEES | LAPLQERCES | LVDIYSQLQQ | EVGAAGGELE | 250 |
| PKTRASLTGR | LDEVLRTLVT | SCFLVEKQPP | QVLKTQTKFQ | AGVRFLLGLR | 300 |
| FLGAPAKPPL | VRADMVTEKQ | ARELSVPQGP | GAGAESTGEI | INNIVPLENS | 350 |
| IPGNCCSALF | KNLLLKKIKR | CERKGTESVT | EEKCAVLFSA | SFTLGPGKLP | 400 |
| IQLQALSLPL | VVIVHGNQDN | NAKATILWDN | AFSEMDRVPF | VVAERVPWEK | 450 |

-continued

| IL-4 Stat protein (SEQUENCE ID NO: 2) | | | | | |
|---|---|---|---|---|---|
| MCETLNLKFM | AEVGINRGLL | PEHFLFLAQK | IFNDNSLSME | AFQHRSVSWS | 500 |
| QFNKEILLGR | GFTFWQWFDG | VLDLTKRCLR | SYWSDRLIIG | FISKQYVTSL | 550 |
| LLNEPDGTFL | LRFSDSEIGG | ITIAHVIRGQ | DGSPQIENIQ | PFSAKDLSIR | 600 |
| SLGDRIRDLA | QLKNLYPKKP | KDEAFRSHYK | PEQMGKDGRG | YVPATIKMIV | 650 |
| ERDQPLPTPE | LQMPTMVPSY | DLGMAPDSSM | SMQLGPDMVP | QVYPPHSHSI | 700 |
| PPYQGLSPEE | SVNVLSAFQE | PHLQMPPSLG | QMSLPFDQPH | PQGLLPCQPQ | 750 |
| EHAVSSPDPL | LCSDVTMVED | SCLSQPVTAF | PQGTWIGEDI | FPPLLPPTEQ | 800 |
| DLTKLLLEGQ | GESGGGSLGA | QPLLQPSHYG | QSGISMSHMD | LRANPSWX | 848 |

What is claimed is:

1. An isolated interleukin-4 signal transducer and activator of transcription (IL-4 STAT) protein wherein said protein:

(a) selectively binds a transcription factor binding site having a sequence selected from the group consisting of SEQ ID NO:03, SEQ ID NO:04, SEQ ID NO:05, SEQ ID NO:06, SEQ ID NO:07, SEQ ID NO:08 and SEQ ID NO:09; and (b) selectively binds an IL-4 receptor peptide having a sequence defined by SEQ ID NO:10 or SEQ ID NO:11; and (c) is encoded by a DNA which hybridizes with SEQ ID NO:01 under high stringency conditions.

2. An isolated interleukin-4 signal transducer and activator of transcription (IL-4 STAT) protein wherein said protein:

(a) selectively binds a transcription factor binding site having a sequence selected from the group consisting of SEQ ID NO:03, SEQ ID NO:04, SEQ ID NO:05, SEQ ID NO:06, SEQ ID NO:07, SEQ ID NO:08 and SEQ ID NO:09; and (b) selectively binds an IL-4 receptor peptide having a sequence defined by SEQ ID NO:10 or SEQ ID NO:11; and (c) is encoded by a DNA which hybridizes with SEQ ID NO:01 under high stringency conditions; and (d) comprises at least one of the amino acid sequences selected from the group consisting of SEQ ID NO:02, residues 1–40 and SEQ ID NO:02, residues 401 to 650.

3. An isolated interleukin-4 signal transducer and activator of transcription (IL-4 STAT) protein wherein said protein:

(a) selectively binds a transcription factor binding site having a sequence selected from the group consisting of SEQ ID NO:03, SEQ ID NO:04, SEQ ID NO:05, SEQ ID NO:06, SEQ ID NO:07, SEQ ID NO:08 and SEQ ID NO:09; and (b) selectively binds an IL-4 receptor peptide having a sequence defined by SEQ ID NO:10 or SEQ ID NO:11; and (c) is encoded by a DNA which hybridizes with SEQ ID NO:01 under high stringency conditions; and (d) comprises the amino acid sequence of SEQ ID NO:02.

* * * * *